United States Patent
Goliszek et al.

(10) Patent No.: US 11,877,788 B2
(45) Date of Patent: Jan. 23, 2024

(54) ELECTROSURGICAL APPARATUS WITH ROBOTIC TIP

(71) Applicant: Apyx Medical Corporation, Clearwater, FL (US)

(72) Inventors: Gregory Goliszek, Oldsmar, FL (US); Shawn D. Roman, Safety Harbor, FL (US)

(73) Assignee: Apyx medical corporation, Clearwater, FL (US)

( * ) Notice: Subject to any disclaimer, the term of this patent is extended or adjusted under 35 U.S.C. 154(b) by 385 days.

(21) Appl. No.: 16/617,534

(22) PCT Filed: May 29, 2018

(86) PCT No.: PCT/US2018/034823
§ 371 (c)(1),
(2) Date: Nov. 27, 2019

(87) PCT Pub. No.: WO2018/222562
PCT Pub. Date: Dec. 6, 2018

(65) Prior Publication Data
US 2020/0085491 A1  Mar. 19, 2020

Related U.S. Application Data

(60) Provisional application No. 62/512,538, filed on May 30, 2017.

(51) Int. Cl.
*A61B 17/3205* (2006.01)
*A61B 18/04* (2006.01)
(Continued)

(52) U.S. Cl.
CPC .......... *A61B 18/14* (2013.01); *A61B 17/3205* (2013.01); *A61B 18/042* (2013.01);
(Continued)

(58) Field of Classification Search
CPC .................. A61B 18/14; A61B 18/042; A61B 2018/1412; A61B 2018/1425;
(Continued)

(56) References Cited

U.S. PATENT DOCUMENTS

| 1,813,902 A | 7/1931 | Bovie |
| 2,435,442 A | 2/1948 | Gurewitsch |

(Continued)

FOREIGN PATENT DOCUMENTS

| CN | 110719759 A | 1/2020 |
| DE | 2429021 A1 | 1/1976 |

(Continued)

OTHER PUBLICATIONS

International Search Report and Written Opinion for PCT Application No. PCT/US2018/034823; dated Aug. 24, 2018; six (6) pages.

(Continued)

*Primary Examiner* — Joseph A Stoklosa
*Assistant Examiner* — Annie L Shoulders
(74) *Attorney, Agent, or Firm* — Michael J Porco; Gerald E Hespos

(57) ABSTRACT

An electrosurgical apparatus including a robotic tip is provided. The electrosurgical apparatus includes a plurality of actuators and hinging members. The robotic tip includes a retractable electrode. The actuators are coupled to the hinging members via a plurality of pulling mechanisms, such that, one or more of the actuators is rotated to selectively pull one or more of the plurality of pulling mechanisms to pivot and rotate the robotic tip and/or extend and retract the electrode. The electrode is coupled to a gas source and an energy source, such that, the electrode can produce plasma for use in surgical applications.

21 Claims, 19 Drawing Sheets

(51) Int. Cl.
*A61B 18/14* (2006.01)
*A61B 17/00* (2006.01)
A61B 34/30 (2016.01)
A61B 18/00 (2006.01)
A61B 18/12 (2006.01)

(52) U.S. Cl.
CPC ..... *A61B 34/30* (2016.02); *A61B 2017/00393* (2013.01); *A61B 2017/00398* (2013.01); *A61B 2017/00973* (2013.01); *A61B 2018/00589* (2013.01); *A61B 2018/00601* (2013.01); *A61B 2018/00642* (2013.01); *A61B 2018/1253* (2013.01); *A61B 2018/144* (2013.01); *A61B 2018/1412* (2013.01); *A61B 2018/1425* (2013.01)

(58) Field of Classification Search
CPC .......... A61B 2018/144; A61B 17/3205; A61B 2017/00393; A61B 2017/00398
See application file for complete search history.

(56) References Cited

U.S. PATENT DOCUMENTS

| | | | |
|---|---|---|---|
| 3,239,730 A | 3/1966 | George |
| 3,801,766 A | 4/1974 | Morrison |
| 4,127,110 A | 11/1978 | Bullara |
| 4,196,734 A | 4/1980 | Harris |
| 4,545,375 A | 10/1985 | Cline |
| 4,580,562 A | 4/1986 | Goof et al. |
| 4,619,258 A | 10/1986 | Pool |
| 4,625,723 A | 12/1986 | Altnether et al. |
| 4,632,109 A | 12/1986 | Paterson |
| 4,708,137 A | 11/1987 | Tsukagoshi |
| 4,827,927 A | 5/1989 | Newton |
| 4,884,557 A | 12/1989 | Takehana et al. |
| 4,905,691 A | 3/1990 | Rydell |
| 4,930,494 A | 6/1990 | Takehana et al. |
| 5,088,997 A | 2/1992 | Delahuerga et al. |
| 5,098,430 A | 3/1992 | Fleenor |
| 5,207,675 A | 5/1993 | Canady |
| 5,254,117 A | 10/1993 | Rigby et al. |
| 5,256,138 A | 10/1993 | Burek et al. |
| 5,257,451 A | 11/1993 | Edwards et al. |
| 5,269,780 A | 12/1993 | Roos |
| 5,306,238 A | 4/1994 | Fleenor |
| 5,400,267 A | 3/1995 | Denen et al. |
| 5,403,342 A | 4/1995 | Tovey et al. |
| 5,413,575 A | 5/1995 | Haenggi |
| 5,425,375 A | 6/1995 | Chin et al. |
| 5,445,635 A | 8/1995 | Denen et al. |
| 5,449,356 A | 9/1995 | Walbrink et al. |
| 5,496,314 A | 3/1996 | Eggers |
| 5,514,157 A | 5/1996 | Nicholas et al. |
| 5,626,575 A | 5/1997 | Crenner |
| 5,647,869 A | 7/1997 | Goble et al. |
| 5,651,780 A | 7/1997 | Jackson et al. |
| 5,660,657 A | 8/1997 | Rajala et al. |
| 5,693,042 A | 12/1997 | Boiarski et al. |
| 5,693,044 A | 12/1997 | Cosmescu |
| 5,697,909 A | 12/1997 | Eggers et al. |
| 5,720,745 A | 2/1998 | Farin et al. |
| 5,743,880 A | 4/1998 | Hlavka |
| 5,776,092 A | 7/1998 | Farin et al. |
| 5,800,427 A | 9/1998 | Zamba |
| 5,908,381 A | 6/1999 | Aznoian et al. |
| 5,916,213 A | 6/1999 | Haissaguerre et al. |
| 5,921,915 A | 7/1999 | Aznoian et al. |
| 5,922,003 A | 7/1999 | Anctil et al. |
| 6,017,340 A | 1/2000 | Cassidy et al. |
| 6,063,081 A | 5/2000 | Mulier et al. |
| 6,099,523 A | 8/2000 | Kim et al. |
| 6,146,380 A | 11/2000 | Racz et al. |
| 6,193,715 B1 | 2/2001 | Wrublewski et al. |
| 6,225,593 B1 | 5/2001 | Howieson et al. |
| 6,231,571 B1 | 5/2001 | Ellman et al. |
| 6,293,945 B1 | 9/2001 | Parins et al. |
| 6,293,960 B1 | 9/2001 | Ken |
| 6,325,799 B1 | 12/2001 | Goble |
| 6,391,027 B1 | 5/2002 | Farin et al. |
| 6,409,724 B1 | 6/2002 | Penny et al. |
| 6,451,016 B1 | 9/2002 | Karakozian |
| 6,458,125 B1 | 10/2002 | Cosmescu |
| 6,475,215 B1 | 11/2002 | Tanrisever |
| 6,508,815 B1 | 1/2003 | Strul et al. |
| 6,558,383 B2 | 5/2003 | Cunningham et al. |
| 6,578,579 B2 | 6/2003 | Burnside et al. |
| 6,652,514 B2 | 11/2003 | Ellman et al. |
| 6,740,079 B1 | 5/2004 | Eggers et al. |
| 6,743,239 B1 | 6/2004 | Kuehn et al. |
| 6,770,071 B2 | 8/2004 | Woloszko et al. |
| 6,852,112 B2 | 2/2005 | Platt |
| 6,899,538 B2 | 5/2005 | Matoba |
| 6,958,063 B1 | 10/2005 | Soll et al. |
| 6,994,707 B2 | 2/2006 | Ellman et al. |
| 7,033,353 B2 | 4/2006 | Stoddard et al. |
| 7,070,596 B1 | 7/2006 | Woloszko et al. |
| 7,115,121 B2 | 10/2006 | Novak |
| 7,156,842 B2 | 1/2007 | Sartor et al. |
| 7,156,844 B2 | 1/2007 | Reschke et al. |
| 7,169,144 B2 | 1/2007 | Hoey et al. |
| 7,244,257 B2 | 7/2007 | Podhajsky et al. |
| 7,306,614 B2 | 12/2007 | Weller et al. |
| 7,316,682 B2 | 1/2008 | Konesky |
| 7,335,199 B2 | 2/2008 | Goble et al. |
| 7,354,435 B2 | 4/2008 | Farin et al. |
| 7,422,585 B1 | 9/2008 | Eggers et al. |
| 7,443,296 B2 | 10/2008 | Mezhinsky et al. |
| 7,479,140 B2 | 1/2009 | Ellman et al. |
| 7,481,809 B2 | 1/2009 | Stern et al. |
| 7,503,917 B2 | 3/2009 | Sartor et al. |
| 7,568,619 B2 | 8/2009 | Todd et al. |
| 7,578,817 B2 | 8/2009 | Canady |
| 7,654,975 B2 | 2/2010 | Mantell |
| 7,749,221 B2 | 7/2010 | Rontal |
| 7,815,638 B2 | 10/2010 | Farin et al. |
| 8,016,824 B2 | 9/2011 | Buchman et al. |
| 8,022,327 B2 | 9/2011 | Blomeyer |
| 8,096,943 B2 | 1/2012 | Melville |
| 8,177,782 B2 | 5/2012 | Beller et al. |
| 8,216,220 B2 | 7/2012 | Jensen et al. |
| 8,319,134 B2 | 11/2012 | Blomeyer |
| 8,328,804 B2 | 12/2012 | Heard et al. |
| 8,337,521 B2 | 12/2012 | Cooper et al. |
| 8,353,905 B2 | 1/2013 | Jensen et al. |
| 8,562,598 B2 | 10/2013 | Falkenstein et al. |
| 8,568,400 B2 | 10/2013 | Gilbert |
| 8,579,802 B2 | 11/2013 | Robertson |
| 8,689,606 B2 | 4/2014 | Schellekens et al. |
| 8,998,899 B2 | 4/2015 | Shilev et al. |
| 9,005,112 B2 | 4/2015 | Hasser et al. |
| 9,060,750 B2 | 6/2015 | Lam |
| 9,060,765 B2 | 6/2015 | Rencher et al. |
| 9,095,333 B2 | 8/2015 | Konesky et al. |
| 9,144,453 B2 | 9/2015 | Rencher et al. |
| 9,326,810 B2 | 5/2016 | Shilev et al. |
| 9,492,219 B2 | 11/2016 | Konesky et al. |
| 9,763,724 B2 | 9/2017 | Konesky et al. |
| 9,770,281 B2 | 9/2017 | Rencher et al. |
| 9,770,285 B2 | 9/2017 | Zoran et al. |
| 10,045,823 B2 * | 8/2018 | Burbank ................ A61B 34/30 |
| 10,064,675 B2 | 9/2018 | Rencher et al. |
| 10,441,369 B2 * | 10/2019 | Shelton, IV ......... A61B 17/295 |
| 11,272,973 B2 | 3/2022 | Gogolin |
| 2001/0025177 A1 | 9/2001 | Woloszko et al. |
| 2002/0013582 A1 | 1/2002 | Mulier et al. |
| 2003/0018318 A1 | 1/2003 | Melsky |
| 2003/0018323 A1 * | 1/2003 | Wallace ................ A61B 34/70 |
| | | 606/1 |
| 2003/0050633 A1 | 3/2003 | Ellman et al. |
| 2003/0130655 A1 | 7/2003 | Woloszko et al. |
| 2004/0148903 A1 | 8/2004 | Cash |
| 2004/0162553 A1 | 8/2004 | Peng et al. |
| 2004/0181150 A1 | 9/2004 | Evans et al. |

(56) References Cited

U.S. PATENT DOCUMENTS

| | | |
|---|---|---|
| 2004/0243120 A1 | 12/2004 | Orszulak et al. |
| 2005/0075630 A1 | 4/2005 | Truckai et al. |
| 2005/0113820 A1 | 5/2005 | Goble et al. |
| 2005/0148903 A1 | 7/2005 | Diamantopoulos |
| 2005/0267459 A1 | 12/2005 | Belhe et al. |
| 2006/0036237 A1 | 2/2006 | Davison et al. |
| 2006/0122595 A1 | 6/2006 | Farin et al. |
| 2006/0161190 A1 | 7/2006 | Gadberry et al. |
| 2007/0010809 A1 | 1/2007 | Hovda et al. |
| 2007/0028669 A1 | 2/2007 | Brewster |
| 2007/0034211 A1 | 2/2007 | Hug et al. |
| 2007/0049922 A1 | 3/2007 | Rontal |
| 2007/0049926 A1 | 3/2007 | Sartor |
| 2007/0083247 A1 | 4/2007 | Wyeth et al. |
| 2007/0093810 A1 | 4/2007 | Sartor et al. |
| 2007/0135812 A1 | 6/2007 | Sartor |
| 2007/0158209 A1 | 7/2007 | Kang et al. |
| 2007/0260239 A1 | 11/2007 | Podhajsky et al. |
| 2007/0270797 A1 | 11/2007 | Lu et al. |
| 2007/0282303 A1 | 12/2007 | Nash et al. |
| 2007/0282358 A1 | 12/2007 | Remiszewski et al. |
| 2008/0071261 A1 | 3/2008 | Orszulak |
| 2008/0108985 A1 | 5/2008 | Konesky |
| 2008/0132893 A1 | 6/2008 | D'Amelio et al. |
| 2008/0140066 A1 | 6/2008 | Davison et al. |
| 2008/0300593 A1 | 12/2008 | Mulier et al. |
| 2009/0005772 A1 | 1/2009 | Penny |
| 2009/0125020 A1* | 5/2009 | Douglass ............ A61B 18/1482 606/41 |
| 2009/0125023 A1 | 5/2009 | Stephen et al. |
| 2009/0143778 A1 | 6/2009 | Sartor et al. |
| 2009/0149851 A1 | 6/2009 | Craig |
| 2009/0171271 A1* | 7/2009 | Webster ............. A61B 17/3421 604/95.01 |
| 2009/0247822 A1 | 10/2009 | Okada et al. |
| 2009/0248022 A1 | 10/2009 | Falkenstein et al. |
| 2009/0253959 A1 | 10/2009 | Yoshie et al. |
| 2009/0270796 A1 | 10/2009 | Perry et al. |
| 2009/0306658 A1* | 12/2009 | Nobis ................ A61B 18/1482 606/46 |
| 2010/0016856 A1 | 1/2010 | Platt, Jr. |
| 2010/0022824 A1 | 1/2010 | Cybulski et al. |
| 2010/0023008 A1 | 1/2010 | Heard et al. |
| 2010/0094288 A1 | 4/2010 | Kerr |
| 2010/0168827 A1 | 7/2010 | Schultz |
| 2010/0262139 A1 | 10/2010 | Beller et al. |
| 2011/0009856 A1 | 1/2011 | Jorgensen et al. |
| 2011/0118601 A1 | 5/2011 | Barnes et al. |
| 2011/0137115 A1 | 6/2011 | Suzuki |
| 2011/0238053 A1 | 9/2011 | Brannan et al. |
| 2011/0276113 A1 | 11/2011 | Cybulski |
| 2012/0046682 A1 | 2/2012 | Nelson et al. |
| 2012/0116397 A1 | 5/2012 | Rencher et al. |
| 2012/0123405 A1 | 5/2012 | Moua et al. |
| 2012/0197246 A1 | 8/2012 | Mauch |
| 2012/0232540 A1 | 9/2012 | Baur et al. |
| 2012/0303016 A1 | 11/2012 | Fischer et al. |
| 2012/0330305 A1 | 12/2012 | Zoran et al. |
| 2012/0330307 A1 | 12/2012 | Ladtkow et al. |
| 2013/0046290 A1 | 2/2013 | Palmer et al. |
| 2013/0218005 A1* | 8/2013 | Desai .................... A61B 6/032 600/424 |
| 2013/0237982 A1 | 9/2013 | Rencher et al. |
| 2013/0253498 A1 | 9/2013 | Germain et al. |
| 2013/0296846 A1 | 11/2013 | Canady et al. |
| 2014/0005665 A1 | 1/2014 | Konesky et al. |
| 2014/0018795 A1 | 1/2014 | Shilev et al. |
| 2014/0236144 A1 | 8/2014 | Krueger et al. |
| 2014/0257276 A1 | 9/2014 | Sartor |
| 2014/0276393 A1* | 9/2014 | Park ................... A61B 18/1492 604/95.01 |
| 2015/0038790 A1 | 2/2015 | Rontal et al. |
| 2015/0073342 A1* | 3/2015 | Pacheco ................ A61B 34/30 604/95.04 |
| 2015/0088060 A1 | 3/2015 | Wang et al. |
| 2015/0209047 A1 | 7/2015 | Whitman |
| 2015/0216582 A1 | 8/2015 | Nagtegaal et al. |
| 2015/0238254 A1 | 8/2015 | Seddon et al. |
| 2015/0335388 A1 | 11/2015 | Iida et al. |
| 2015/0366602 A1 | 12/2015 | Rencher et al. |
| 2016/0022347 A1* | 1/2016 | Rencher ................ A61B 18/14 606/42 |
| 2016/0128766 A1* | 5/2016 | Hyodo .................. A61B 34/30 606/41 |
| 2016/0228171 A1 | 8/2016 | Boudreaux |
| 2016/0331438 A1 | 11/2016 | Staneker et al. |
| 2017/0273733 A1* | 9/2017 | Weber ................ A61B 18/1402 |
| 2018/0014869 A1 | 1/2018 | Gogolin |
| 2018/0146925 A1 | 5/2018 | Mogul |
| 2020/0085491 A1 | 3/2020 | Goliszek et al. |

FOREIGN PATENT DOCUMENTS

| | | |
|---|---|---|
| DE | 9117111 | 11/1995 |
| DE | 102010061059 A1 | 4/2012 |
| EP | 0186369 A1 | 7/1986 |
| EP | 0878263 A1 | 11/1998 |
| EP | 1764057 A1 | 3/2007 |
| EP | 1764057 B1 | 4/2009 |
| EP | 2263728 A2 | 12/2010 |
| EP | 2449992 A1 | 5/2012 |
| JP | 2007068596 A | 3/2007 |
| WO | 03001986 A2 | 1/2003 |
| WO | WO03001986 | 1/2003 |
| WO | 03082134 A1 | 10/2003 |
| WO | 2004096315 A2 | 11/2004 |
| WO | 2018222562 A1 | 12/2018 |

OTHER PUBLICATIONS

EP Search Report and Written Opinion for EP Application No. 18 809 601.0; dated Jan. 20, 2021; nine (9) pages.

* cited by examiner

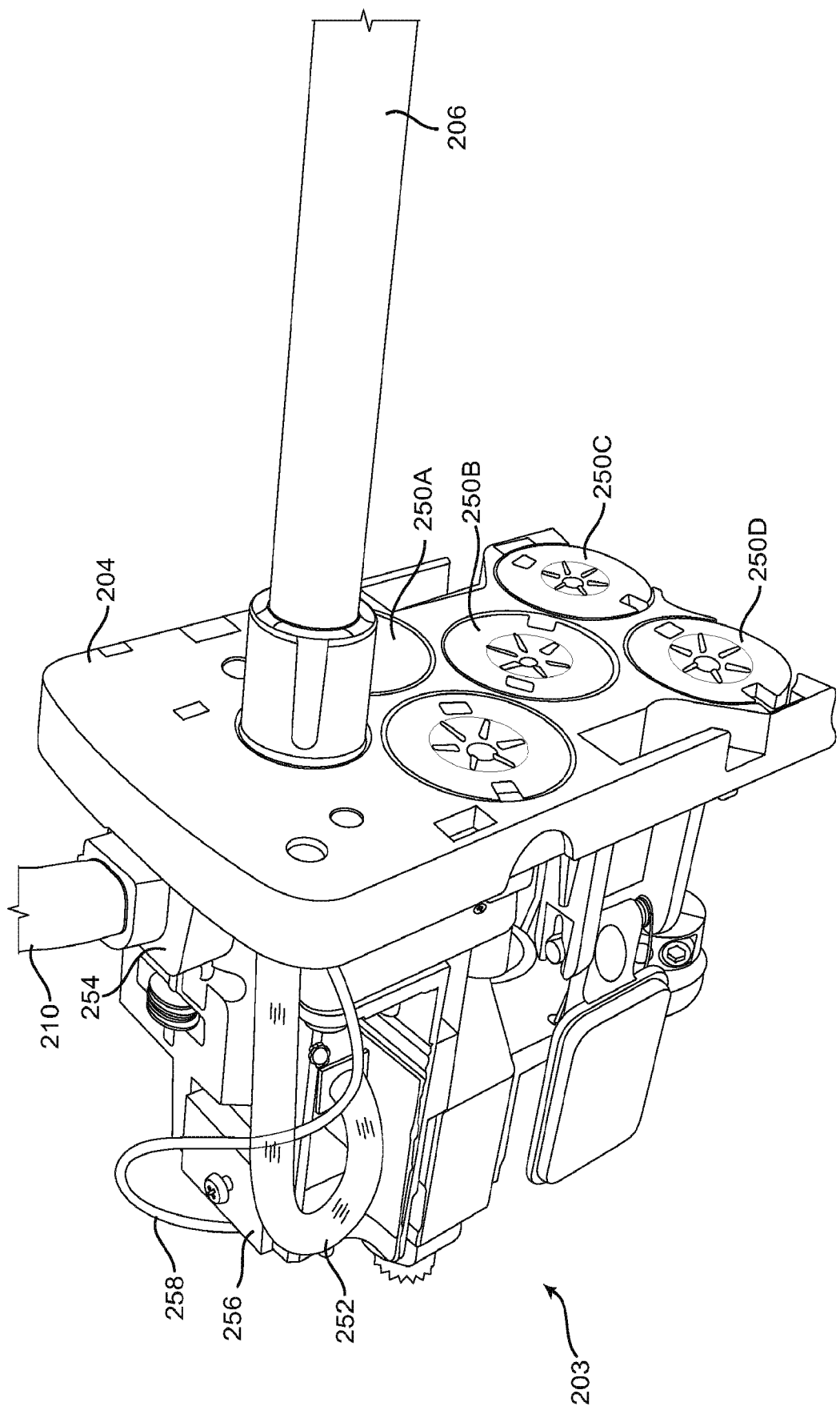

ELECTROSURGICAL APPARATUS WITH ROBOTIC TIP

PRIORITY

This application claims priority to U.S. Provisional Patent Application No. 62/512,538, filed May 30, 2017, entitled "ELECTROSURGICAL APPARATUS WITH ROBOTIC TIP", the contents of which are hereby incorporated by reference in its entirety.

BACKGROUND

Field

The present disclosure relates generally to electrosurgery and electrosurgical systems and apparatuses, and more particularly, to an electrosurgical apparatus with a robotic tip and a retractable electrode for use in cold plasma applications, electrosurgical cutting and mechanical cutting.

Description of the Related Art

High frequency electrical energy has been widely used in surgery and is commonly referred to as electrosurgical energy. Tissue is cut and bodily fluids are coagulated using electrosurgical energy.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes. Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

Atmospheric pressure discharge cold plasma applicators have found use in a variety of applications including surface sterilization, hemostasis, and ablation of tumors. Often, a simple surgical knife is used to excise the tissue in question, followed by the use of a cold plasma applicator for cauterization, sterilization, and hemostasis. Cold plasma beam applicators have been developed for both open and endoscopic procedures. In the latter case, it is often desirable to be able to redirect the position of the cold plasma beam tip to a specific operative site. The external incision and pathway for the endoscopic tool may be chosen to avoid major blood vessels and non-target organs, and may not coincide with an optimum alignment for the target internal tissue site. A means of redirecting the cold plasma beam is essential in these situations.

Elaborate mechanisms have been developed to change the direction of the plasma beam by the surgeon as needed. However, these mechanisms are mechanically complicated, expensive to produce and, in some cases, unwieldy to operate effectively. The small diameter of the endoscopic trocar through which this surgical tool must be inserted places even more severe restrictions on these issues.

SUMMARY

The present disclosure relates to an electrosurgical apparatus with a retractable electrode, e.g., a blade, needle, sharp electrode, etc., for use in cold plasma applications, electrosurgical cutting and mechanical cutting.

In one aspect, the electrosurgical apparatus of the present disclosure includes a robotic tip for pivoting and rotating the orientation of the retractable electrode in a variety of ways.

According to one aspect of the present disclosure, an electrosurgical apparatus includes an assembly including at least one actuator; a shaft including a proximal end, a distal end, and a hollow interior, the proximal end of the shaft coupled to the assembly; a tip including an electrode housing and a hinging mechanism coupling the electrode housing to the distal end of the shaft, the electrode housing including a proximal end and a distal end, an electrode being disposed through the distal end of the electrode housing; and a plurality of pulling mechanisms, each of pulling mechanism disposed through the hollow interior of the shaft and including a proximal end and a distal end, the proximal end of each pulling mechanism coupled to a respective one of the at least one actuator and the distal ends of each pulling mechanism coupled to the proximal end of the electrode housing, wherein the at least one actuator is configured to be rotated to selectively pull one or more of the pulling mechanisms in a proximal direction to pivot the tip relative to the shaft via the hinging mechanism.

In one aspect, the hinging mechanism includes a first hinging member and a second hinging member, the first and second hinging members hingedly coupled to each other such that, responsive to the selective pulling of one or more of the pulling mechanisms, the tip is pivoted relative to the shaft along a first two-dimensional plane.

In another aspect, the hinging mechanism includes a third hinging member, the third hinging member hingedly coupled to the second hinging member such that, responsive to the selective pulling of one or more of the pulling mechanisms, the tip is pivoted relative to the shaft along a second two-dimensional plane.

In a further aspect, the hinging mechanism is configured such that the tip is pivotable relative to the shaft via the hinging mechanism in three dimensions.

In another aspect, the at least one actuator includes a first actuator and a second actuator and the plurality of pulling mechanisms include first, second, third, and fourth pulling mechanisms, the proximal ends of the first and second pulling mechanisms coupled to the first actuator such that when the first actuator is rotated, one of the first or second pulling mechanisms is pulled in a proximal direction and tension from the other of the first or second pulling mechanisms is released enabling the other of the first or second pulling mechanisms to travel in a distal direction, the proximal ends of the third and fourth pulling mechanisms coupled to the second actuator such that when the second actuator is rotated, one of the third or fourth pulling mechanisms is pulled in a proximal direction and tension from the other of the third or fourth pulling mechanisms is released enabling the other of the third or fourth pulling mechanisms to travel in a distal direction.

In yet another aspect, when equal tension is maintained in each of the plurality of pulling mechanisms, the tip is colinear relative to the shaft.

In one aspect, each pulling mechanism includes a first wire, a second wire, and a rigid linear member, the first wire coupled to the proximal end of the electrode housing, the rigid linear member coupling the first wire to the second wire, and the second wire coupled to the at least one actuator.

In a further aspect, the electrosurgical apparatus further includes a tube including a proximal end and a distal end, the tube disposed through the hollow interior of the shaft, the distal end of the tube coupled to the proximal end of electrode housing and the proximal end of the tube configured to receive a gas to be provided to the electrode housing.

In still another aspect, the hinging mechanism includes at least one aperture, the distal end of the tube disposed through the at least one aperture and coupled to the proximal end of the electrode housing.

In another aspect, the electrosurgical apparatus further includes a conductive wire including a proximal end and a distal end, the proximal end of the conductive wire is coupled to the electrode to provide electrosurgical energy thereto.

In yet another aspect, the conductive wire is slidable within the shaft and the electrosurgical apparatus further comprises at least one second actuator, the at least one second actuator coupled to the conductive wire and configured to be rotated to control the extension and retraction of the electrode relative to the distal end of the electrode housing.

In one aspect, when the electrode is extended past the distal end of the electrode housing or the electrode is retracted within the electrode housing, the electrode is energized via the conductive wire and gas is provided to the electrode housing to form plasma.

In another aspect, the electrode is extended past the distal end of the electrode housing for mechanical cutting.

In still a further aspect, the electrode is extended past the distal end of the electrode housing and the electrode is energized via the conductive wire for electrosurgical cutting.

According to a further aspect of the present disclosure, the electrosurgical apparatus further includes a sliding member slidably mounted within the assembly, the sliding member coupled to the distal end of the conductive wire and to the second actuator, wherein, responsive to the rotation of the second actuator in a first direction, the sliding member is configured to pull the conductive wire in the proximal direction to retract the electrode relative to the distal end of the electrode housing.

In one aspect, the electrosurgical apparatus further includes a spring disposed in the electrode housing, the spring configured to bias the electrode in a distal direction past the distal end of the electrode housing.

In a further aspect, responsive to the rotation of the second actuator in a second direction, the sliding member is configured to extend the conductive wire in a distal direction to extend the electrode relative to the distal end of the electrode housing.

In another aspect, the sliding member is coupled to a gas source and to the tube and the sliding member is configured to provide the gas from the gas source to the tube.

In still another aspect, the sliding member is coupled to an energy source and the sliding member is configured to provide electrosurgical energy to the conductive wire.

In one aspect, the electrosurgical apparatus further includes a second actuator, the second actuator coupled to the shaft such that rotation of the second actuator rotates the shaft relative to the assembly, wherein when the shaft is rotated, the tip is rotated.

In a further aspect, the electrode is configured as one of an electrically conducting blade or an electrically conductive needle.

In yet another aspect, the at least one actuator is configured to be coupled to at least one motor for rotating the at least one actuator, the at least one motor is configured to be controlled via at least one processor and at least one input receiving device.

In one aspect, the electrosurgical apparatus further includes a third actuator, the third actuator coupled to the shaft such that rotation of the third actuator rotates the shaft relative to the assembly, wherein when the shaft is rotated, the tip is rotated.

In another aspect, the electrosurgical apparatus further includes a fourth actuator and a wire, the wire disposed through the shaft and coupling the fourth actuator to the electrode, the fourth actuator configured to be rotated to control the extension and retraction of the electrode relative to the distal end of the electrode housing.

In a further aspect, each actuator is coupled to a corresponding motor, each motor is controllable via at least one processor and at least one input receiving device to selectively rotate one or more of the actuators to pivot the tip relative to the shaft, rotate the tip and shaft relative to the assembly, and/or extend or retract the electrode relative to the distal end of the electrode housing.

BRIEF DESCRIPTION OF THE DRAWINGS

The above and other aspects, features, and advantages of the present disclosure will become more apparent in light of the following detailed description when taken in conjunction with the accompanying drawings in which:

FIGS. 3B-E are perspective views of the assembly of FIG. 3A with a housing of the assembly removed in accordance with an embodiment of the present disclosure;

Figure 1:
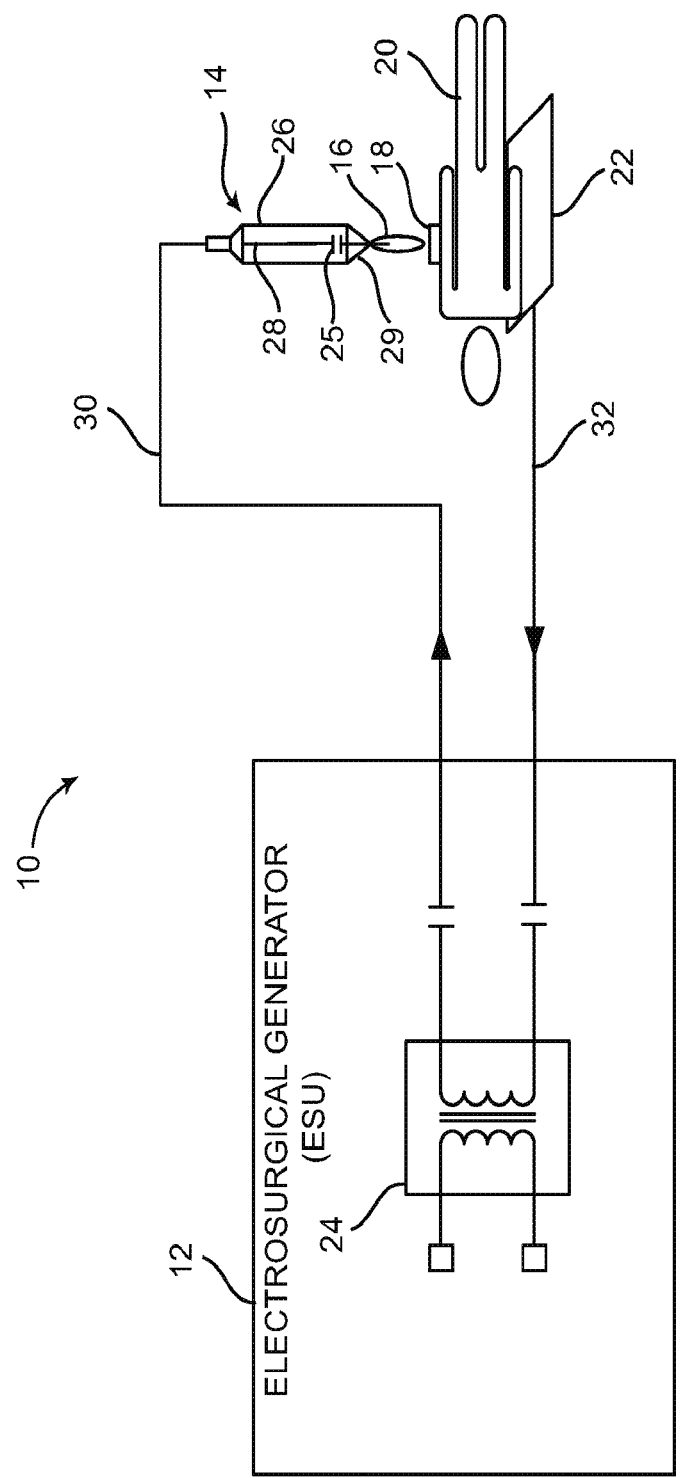
FIG. 1 is an illustration of an exemplary monopolar electrosurgical system in accordance with an embodiment of the present disclosure.

It should be understood that the drawings are for purposes of illustrating the concepts of the disclosure and are not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

FIG. 1 shows an exemplary monopolar electrosurgical system generally indicated as 10 comprising an electrosurgical generator (ESU) generally indicated as 12 to generate power for the electrosurgical apparatus 10 and a plasma generator generally indicated as 14 to generate and apply a plasma stream 16 to a surgical site or target area 18 on a patient 20 resting on a conductive plate or support surface 22. The electrosurgical generator 12 includes at least one transformer generally indicated as 24 that may include a primary and secondary coupled to an electrical source (not shown) to provide high frequency electrical energy to the plasma generator 14. In one embodiment, the electrosurgical generator 12 comprises an isolated floating potential not referenced to any potential. Thus, current flows between the active and return electrodes. If the output is not isolated, but referenced to "earth", current can flow to areas with ground potential. If the contact surface of these areas and the patient is relatively small, an undesirable burning can occur.

The plasma generator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma stream 16. In some embodiments, electrode 28 is configured to be retractable, such that the electrode 28 may be advanced to extend outside of housing 29 or be retracted within housing 29. The high frequency electrical energy is fed from the secondary of the transformer 24 through an active conductor 30 to the electrode 28 (collectively active electrode) in the handpiece 26 to create the plasma stream 16 for application to the surgical site 18 on the patient 20. Furthermore, a current limiting capacitor 25 may be provided in series with the electrode 28 to limit the amount of current being delivered to the patient 20.

The return path to the electrosurgical generator 12 is through the tissue and body fluid of the patient 20, the conductor plate or support member 22 and a return conductor 32 (collectively return electrode) to the secondary of the transformer 24 to complete the isolated, floating potential circuit.

In another embodiment, the ESU 12 comprises an isolated non-floating potential not referenced to any potential. The plasma current flow back to the ESU 12 is through the tissue and body fluid and the patient 20. From there, the return current circuit is completed through the combined external capacitance to the plasma generator handpiece 26, surgeon and through displacement current. The capacitance is determined, among other things, by the physical size of the patient 20. Such an electrosurgical apparatus and generator are described in commonly owned U.S. Pat. No. 7,316,682 to Konesky, the contents of which are hereby incorporated by reference in its entirety.

It is to be appreciated that in some embodiments ESU 12 may be configured for use with a handpiece 26 that does not include a dedicated transformer. In this embodiment, ESU 12 includes at least one second transformer configured to perform at least some of the tasks that a transformer within handpiece 26 would perform. In this embodiment, the ESU 12 is configured for use with a handpiece 26 that does not include a dedicated transformer, such that ESU 12, is configured to support a new plasma mode, herein called internal J-Plasma mode, or simply J-Plasma mode. J-Plasma mode is designed to allow a handpiece 26 to generate plasma without requiring handpiece 26 to include an internal transformer.

It is to be appreciated that in the embodiment described above, where the handpiece 26 does not include a dedicated transformer, current limiting capacitor 25 may be removed from handpiece 26. In this embodiment, ESU 12 may be configured for use with handpiece 26 as a closed-loop system, where ESU 12 can effectively limit the current delivered to electrode 28 without the need for handpiece 26 to include an internal dedicated transformer.

The ESU 12 of the present disclosure may be configured to generate various different plasma beam effects by modifying the applied high voltage and high frequency waveform of the power provided to electrode 28 by ESU 12. In addition to the generation of cold plasma, these effects include several forms of monopolar coagulation and gas assisted coagulation, also known as Cool Coag™ effects. It is to be appreciated that in these gas assisted coagulation modes a coagulation waveform is applied to the electrode while an inert gas is present, e.g., Helium, thereby forming a plasma. In this manner, a single electrosurgical apparatus in accordance with the present disclosure may generate 1.) cold plasma discharges, 2.) monopolar coagulation effects and 3.) various gas assisted coagulation discharges, or plasma.

It is to be appreciated that in various embodiments two high voltage step up output transformers are included in ESU 12 and are utilized to generate the necessary waveforms. An exemplary system including two high voltage step up output transformers are shown and described in commonly owned U.S. Pat. No. 9,144,453 to Rencher, et al., the contents of which are hereby incorporated by reference. One transformer is optimized for high voltage and low current and is utilized in generating the cold plasma beam with the electrode retracted (such as with electrode 28 and/or electrode 240, described below). The other transformer is optimized for somewhat lower voltage but higher current required by electrosurgical procedures such as monopolar, bipolar, and coagulation. Buttons on a hand held applicator, such as applicator 14, or selection of an appropriate foot switch or pedal coupled to ESU 12, may be configured to control which transformer in ESU 12 is activated for the required procedure to activate the various modes ESU 12 provides for.

In the monopolar coagulation mode, (e.g., activated by pressing an appropriate foot switch, as described above), a coagulation waveform is applied to the electrode and coagulation effects may be applied to target tissue by making contact between the electrode of the electrosurgical device and the target tissue.

In the plasma coagulation mode, (e.g., activated by a button or an appropriate foot switch of the electrosurgical apparatus, as described above) several forms of gas assisted coagulation (or plasma coagulation) can be affected by spacing the electrode a predetermined distance away from the target tissue, including a pinpoint coagulation mode, a gentle coagulation mode, and a spray coagulation mode. A high crest factor, or ratio of peak voltage to RMS voltage, assures ignition of the flowing inert gas in the various gas assisted coagulation modes. In one embodiment, the coagulation mode to be employed during plasma coagulation (e.g., when an appropriate foot switch or pedal is pressed) is selected at an electrosurgical generator that is providing electrosurgical energy to the apparatus. In this way, after a coagulation mode is selected at the generator (e.g., pinpoint, gentle, or spray coagulation mode), when a coagulation button or foot switch of the electrosurgical apparatus (e.g., applicator 14 or apparatus 200 described below) is activated, the selected coagulation mode is employed in the plasma beam emitted by the electrosurgical apparatus.

In the pinpoint and gentle gas assisted coagulation modes, a relatively short period exists between the plasma generating pulse groups. Residual ions from the previous discharge path ensure that subsequent discharges follow the same path, providing a plasma beam with the same pointing accuracy as the cold plasma beam, but with substantially higher current and enhanced coagulation capability.

The gas assisted spray mode, by contrast, has a much longer period between pulses (e.g., by applying the fulguration mode waveform to the electrode), permitting any residual ions to recombine. There is, therefore, no preferential residual discharge path and the individual discharges randomly cover a much larger area.

As in the cold plasma beam mode, a wide range of physiological effects can be affected in the various gas assisted coagulation modes by adjusting the ratio of electrical power in the beam and the inert gas flow rate.

From the above, it is to be appreciated that a single electrosurgical apparatus (e.g., applicator 14 and/or apparatus 200, described below) in accordance with the present disclosure may include at least three activation modes including a cold plasma mode, a monopolar coagulation mode (where an electrode of the electrosurgical apparatus is touching target tissue) and a gas assisted or plasma coagulation mode (where an electrode of the electrosurgical apparatus is spaced apart from the target tissue without touching the tissue).

Figure 2:
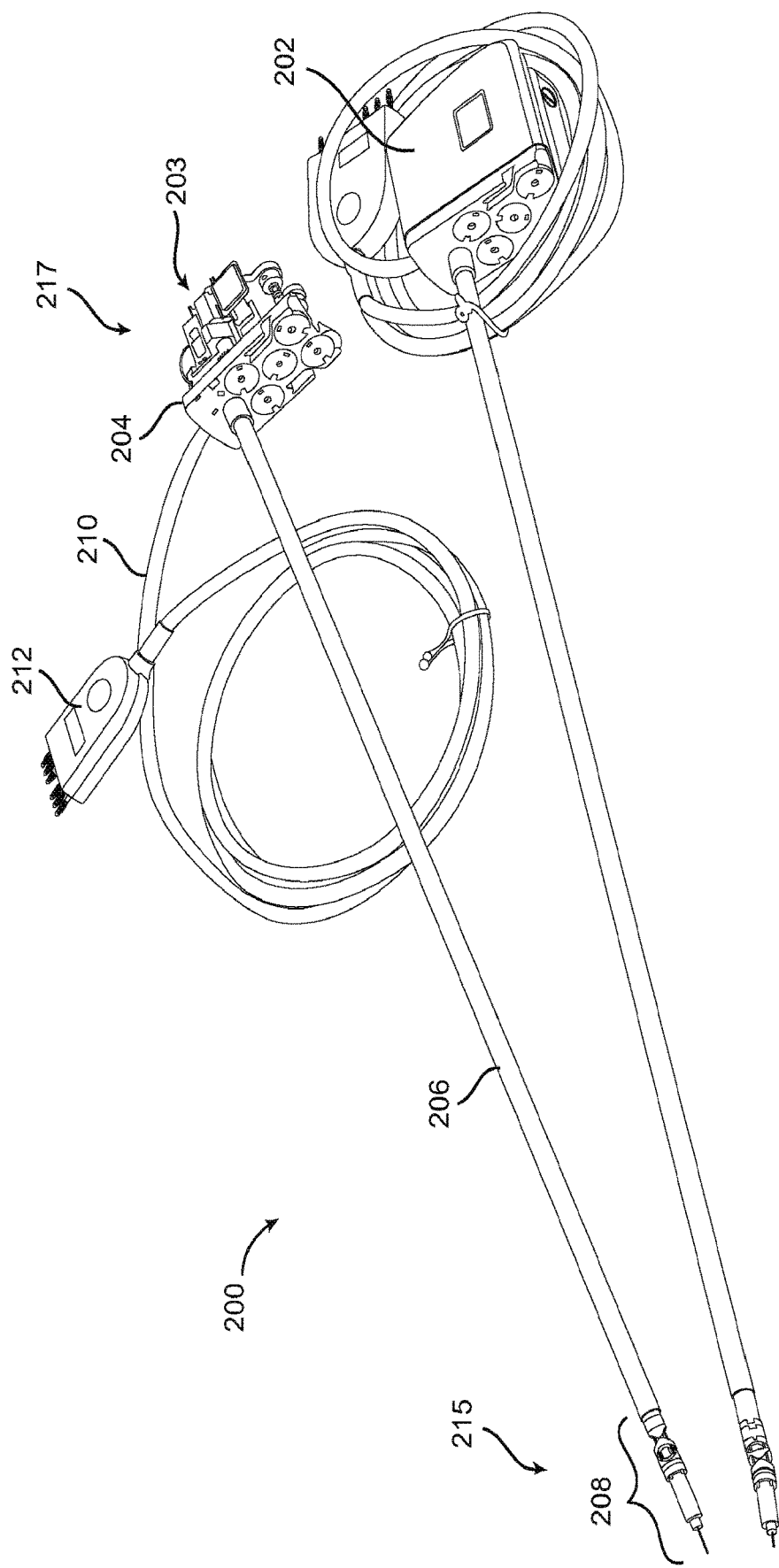
FIG. 2 is a perspective view of an electrosurgical device with a robotic tip in accordance with an embodiment of the present disclosure.

In another embodiment, the present disclosure provides an electrosurgical apparatus including an articulating distal end configured to be pivoted and rotated in a plurality of directions. The electrosurgical apparatus of the present disclosure is configured to be used in robotic surgical systems to perform a wide variety of surgeries, as will be described below. Referring to FIG. 2, an electrosurgical apparatus 200 with a robotic distal tip 208 is shown in accordance with the present disclosure. Apparatus 200 includes a distal end 215 and a proximal end 217, where an assembly 203 is disposed at proximal end 217 of apparatus 200. Assembly 203 includes a housing 202 and a base 204, where housing 202 is coupled to base 204. As will be described in greater detail below, one or more components of apparatus 200 are coupled to base 204 and disposed within housing 202. A shaft 206 and a cable 210 are each coupled to assembly 203. Cable 210 is further coupled to connector 212 and shaft 206 is further coupled to robotic distal tip 208. It is to be appreciated that FIG. 2 illustrates the apparatus 220 with the housing 202 in a lower portion of the figure, while the upper portion of FIG. 2 illustrates the same apparatus 200 with the housing removed.

In one embodiment, connector 212 is configured to be coupled to an ESU, such as ESU 12, and a gas supply. It is to be appreciated that in some embodiments, the ESU includes the gas supply. The ESU and gas supply coupled to connector 212 provide electrosurgical energy and gas via cable 210 to assembly 203. In one embodiment, cable 210 may include one or more flexible gas tubes configured to carry gas from a gas source or supply to assembly 203 and one or more electrically conducting wires configured to provide electrical power and carry electrical signals from the ESU (or any other device coupled to assembly 203 via cable 210) to assembly 203. Gas and electrosurgical energy is provided from assembly 203 to robotic distal tip 208 via shaft 206. Tip 208 may include a retractable electrode or blade, which, in combination with the electrosurgical energy and gas provided via assembly 203 may be used to produce a plasma beam for surgical applications. Assembly 203 includes one or more actuators configured to rotate and pivot robotic distal tip 208 in a plurality of ways. At least one of the actuators may also be used to extend or retract the electrode in robotic tip 208. It is to be appreciated that each of the features of apparatus 200 are described in greater detail below.

Figure 3A:
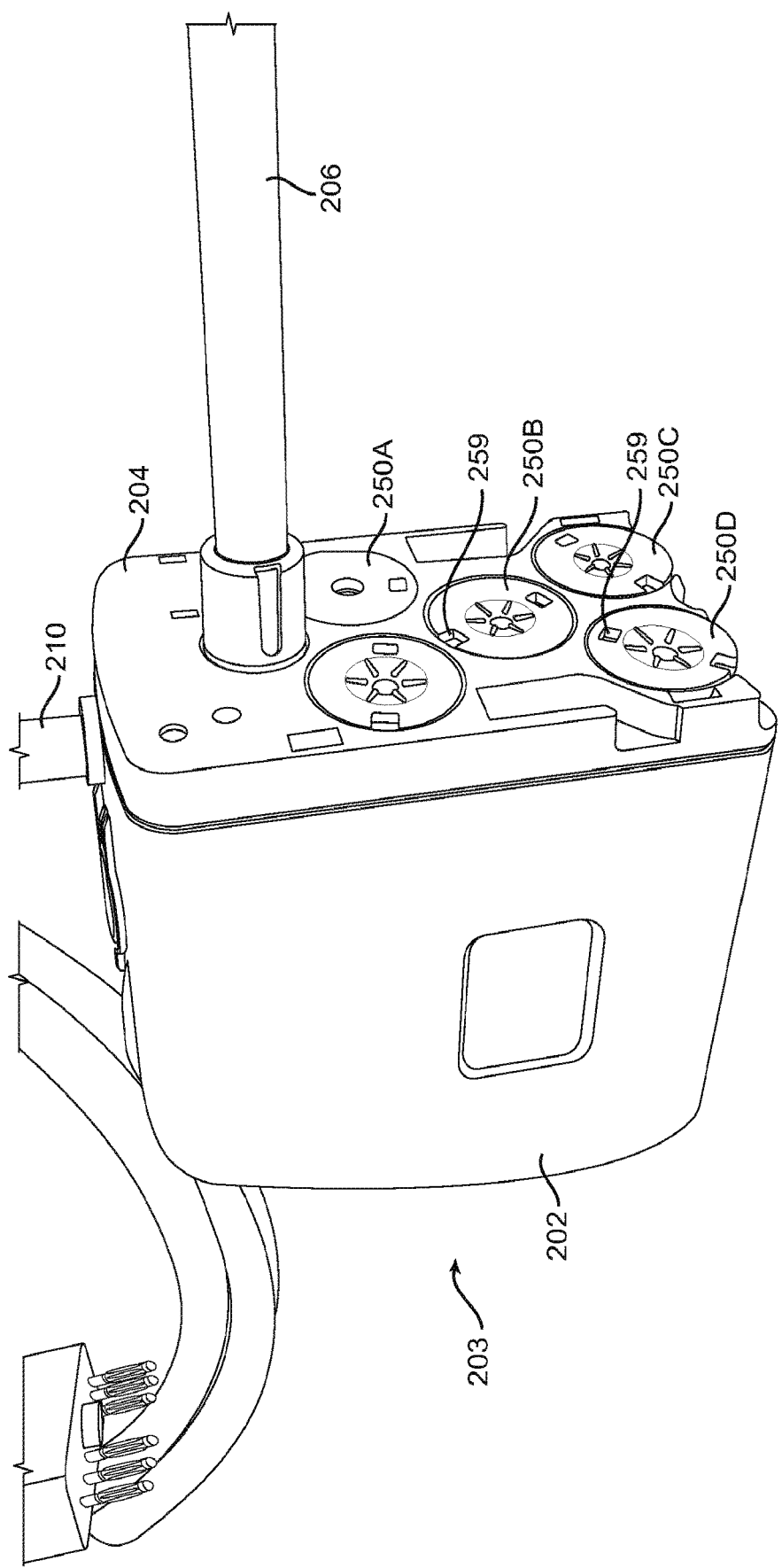
FIG. 3A is a perspective view of an assembly of the electrosurgical device of FIG. 2 in accordance with an embodiment of the present disclosure.

Referring to FIGS. 3A to 3E, various views of assembly 203 are shown in accordance with the present disclosure. As shown in FIGS. 3A and 3B, shaft 206 is coupled to and extends from base 204 along a longitudinal axis. In one embodiment, shaft 206 is a rigid carbon fiber tube including a hollow interior. Also, a plurality of actuators 250 are coupled to base 204. In one embodiment, each of actuators 250 are configured as interfaces that can each be coupled to a motor of an apparatus controllable by a user. In one embodiment, each actuator 250 may include one or more slots 259 configured to receive a tab or extension member of a mating disk of a motor to couple each actuator 250 to a respective motor. In this way, when the mating disk (or any other mating mechanism for coupling a motor to one of actuators 250) of a motor coupled to an actuator 250 is rotated, the actuator 250 is also rotated.

The rotations of actuators control and manipulate the orientation of robotic tip 208. For example, as will be described in greater detail below, actuator 250A may be configured to control the rotation of shaft 206 to cause the rotation of robotic tip 208, actuator 250B may be configured to control the extension and retraction of an electrode or blade of robotic tip 208 (e.g., electrode 240 described below), and actuators 250C and 250D may be configured to control the pivoting of robotic tip 208 about one or more hinging members.

Figure 3C:
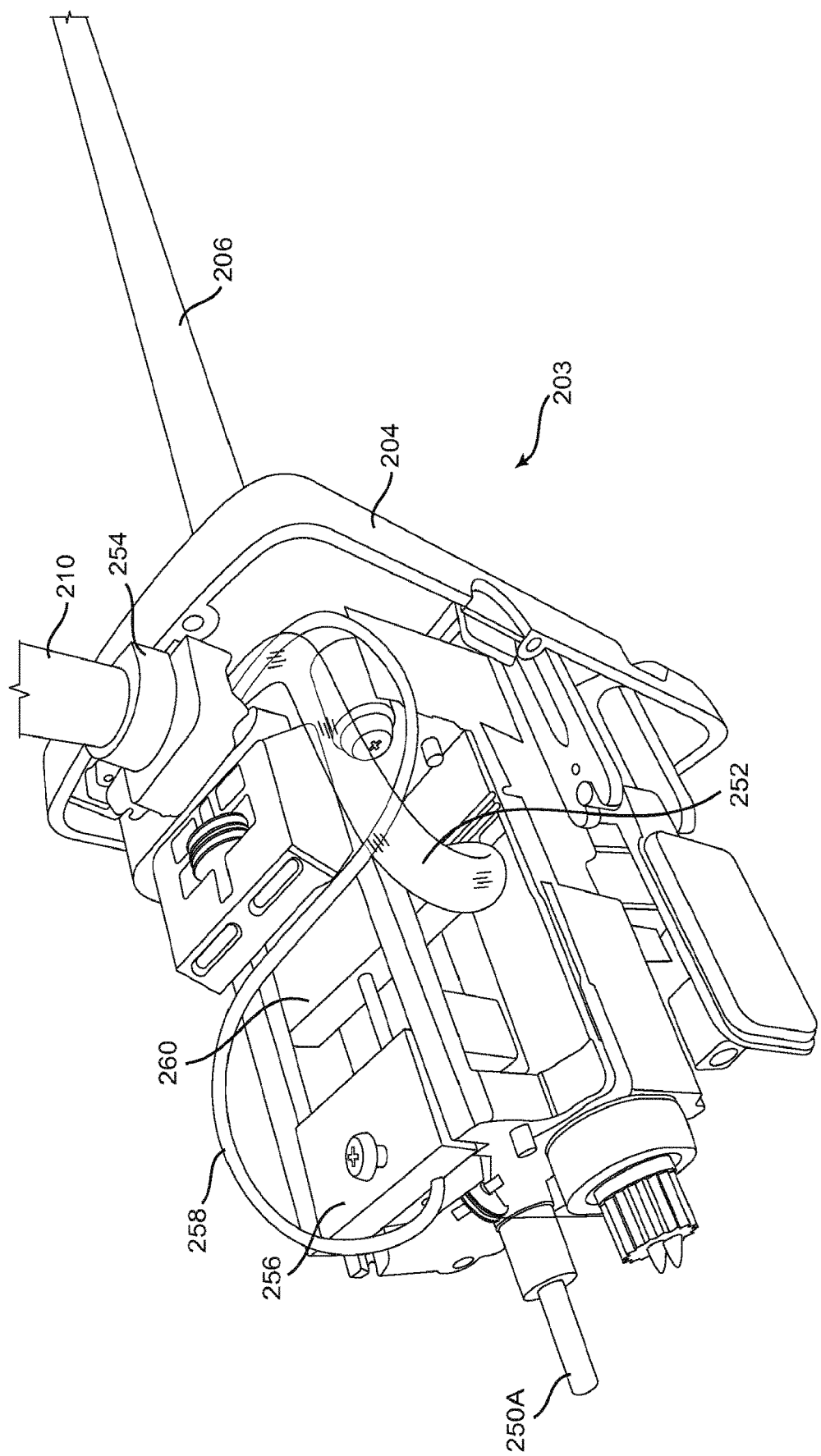
Figure 3D:
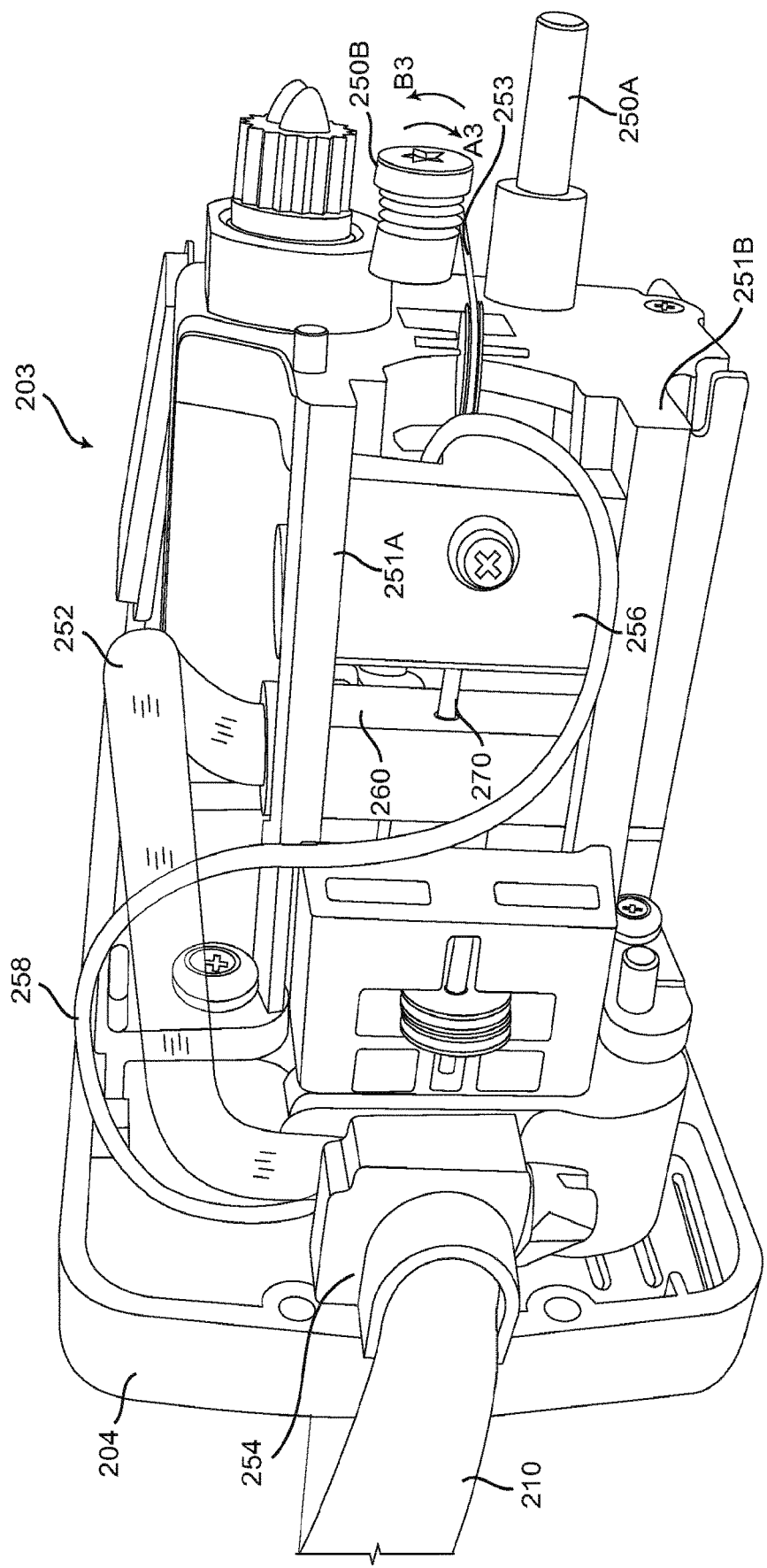

Referring to FIGS. 3B, 3C, and 3D, cable 210 is coupled to assembly 203 via a cable holder 254. Cable holder 254 is configured to provide strain relief for cable 210. Cable holder 254 is coupled to gas port 252 (e.g., a flexible tube suitable for carrying gas), where gas port 252 is further coupled to tube sealing block 260. Cable holder 254 is also coupled to cable 258, where cable 258 is coupled to interfacing block or sliding member 256. It is to be appreciated that a gas tube disposed within cable 210 and configured to carry gas from a gas source to assembly 203 is coupled to gas port 252. In one embodiment, gas port 252 is a single gas tube disposed through cable 210 and coupled to the gas source. It is also to be appreciated that one or more electrical wires disposed in cable 210 and configured to carry electrical power from an ESU to assembly 203 are coupled to cable 258. In one embodiment, cable 258 is disposed through cable 210 and coupled to the ESU.

In one embodiment, tube sealing block 260 is fixedly mounted to assembly 203 via brackets 251A and 251B (shown in FIG. 3D) and interfacing block 256 is slidably mounted to assembly 203 via brackets 251A and 251B, such that, interfacing block 256 may be advanced in a distal direction toward tube sealing block 260 or retracted in a proximal direction away from tube sealing block 260. It is to be appreciated that interfacing block 256 is coupled to a conductive wire or rod 270 (shown in FIGS. 3D and 4) disposed through shaft 206 and coupled to an electrode of tip 208, such that, as interfacing block 256 is advanced in a distal direction toward tube sealing block 260 or retracted in a proximal direction away from tube sealing block 260, wire 270 causes the electrode of tip 208 to also be advanced or retracted in the same direction as the movement of interfacing block 256. In one embodiment, wire 270 is a flexible stainless steel conducting wire of 0.30 mm thickness configured to reduce leakage capacitance while still being sufficiently rigid to advance or retract the electrode within tip 208.

Figure 4:
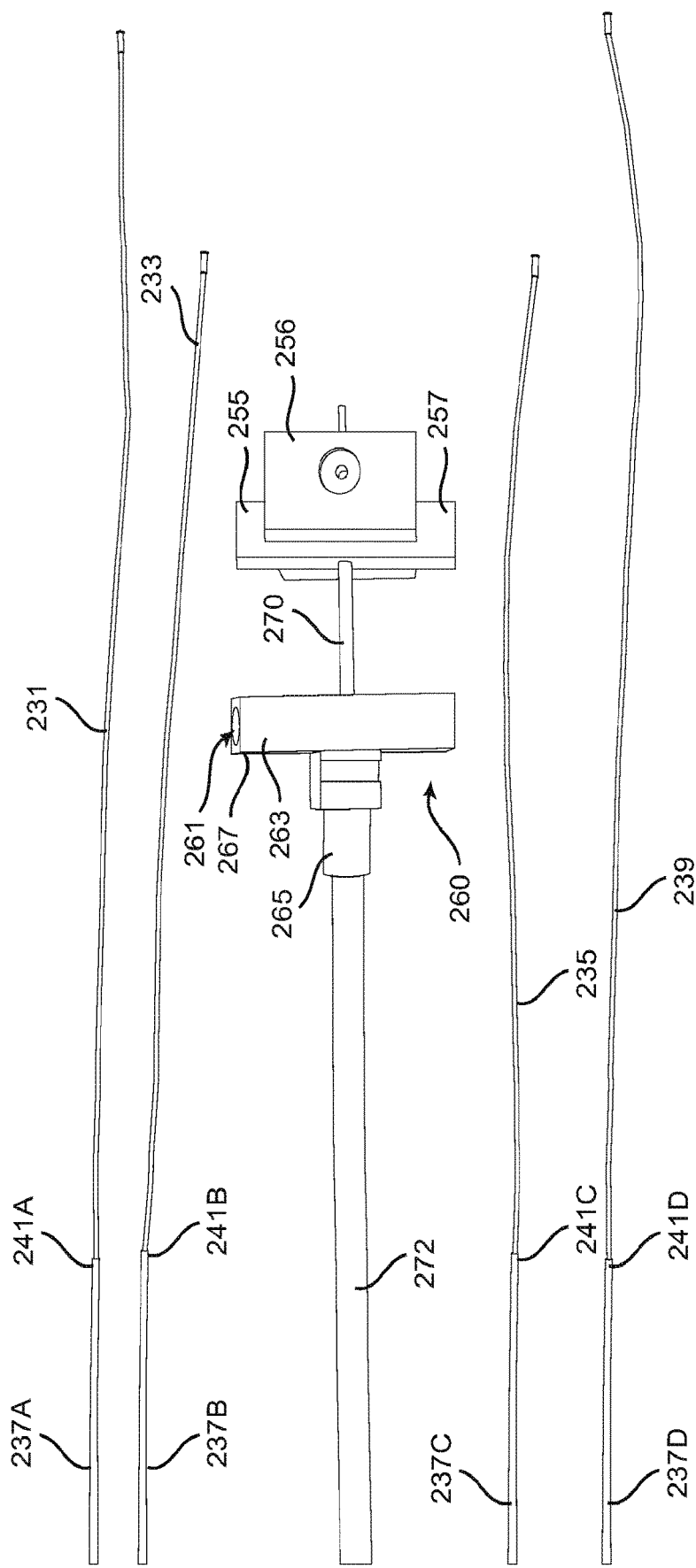
FIG. 4 is a side view of several components of the electrosurgical apparatus of FIG. 2 in accordance with an embodiment of the present disclosure.

For example, referring to FIG. 4, blocks 260 and 256 are shown in greater detail in accordance with the present disclosure. As shown in FIG. 4, tube sealing block 260 includes a tube receiving member 265 and a block portion 263, where tube receiving member 265 extends from block portion 263 in a direction toward base 204. Tube receiving member 265 is configured in a generally cylindrical shape with a hollow interior or inner channel. Block portion 263 includes a channel 261, where channel 261 extends from an end 267 of block portion 263 into tube receiving member 265 such that channel 261 and the inner channel of tube receiving member 265 merge. Gas port 252 is coupled to channel 261 via end 267 of block portion 263. Tube receiving member 265 is configured to receive a proximal end of a flexible tube 272, e.g., a flexible Teflon tube. A distal end of tube 272 is coupled to tip 208 (described below). Gas is provided from a gas supply coupled to apparatus 200 via cable 210, through gas port 252, through channel 261 of gas sealing block 260, through an inner channel of tube 272 to tip 208. As will be described below, the gas may be an inert gas, such as helium, that is used in combination with an electrode 240 of tip 208 to generate plasma.

Also shown in FIG. 4, interfacing block 256 includes ends 255 and 257, where end 255 is slidably disposed in a slot of bracket 251A and end 257 is slidably disposed in a slot of bracket 251B. It is to be appreciated that brackets 251A and 251B are shown in FIG. 3D. A distal end of wire 270 (e.g., a conducting wire) is fixedly coupled to interfacing block 256 (e.g., via a screw or other fastening means). Wire 270 is slidably disposed through an aperture (not shown) of block portion 263 of gas tube sealing block 260, through tube the inner channel of receiving member 265, and into the interior of gas tube 272. As described below, a distal end of wire 270 is fixedly coupled to electrode 240, such that, as interfacing block 256 is advanced toward tube sealing block 260 or away from tube sealing block 260, wire 270 also slides within tube sealing block 260 and tube 272 in a direction toward or away from tube sealing block 260 to cause electrode 240 of tip 208 to be advanced or retracted. In one embodiment, cable 258 of assembly 203 couples cable 210 to wire 270, such that, electrosurgical energy can be provided by ESU 12 to wire 270 (via cable 258) to energize electrode 240 of tip 208.

Although in the embodiments described above, tube sealing block 260 and interfacing block 256 are configured as separate components, as will be described below, in other embodiments of the present disclosure, interfacing block 256 and tube sealing block 260 may be configured as a single component.

Figure 3E:
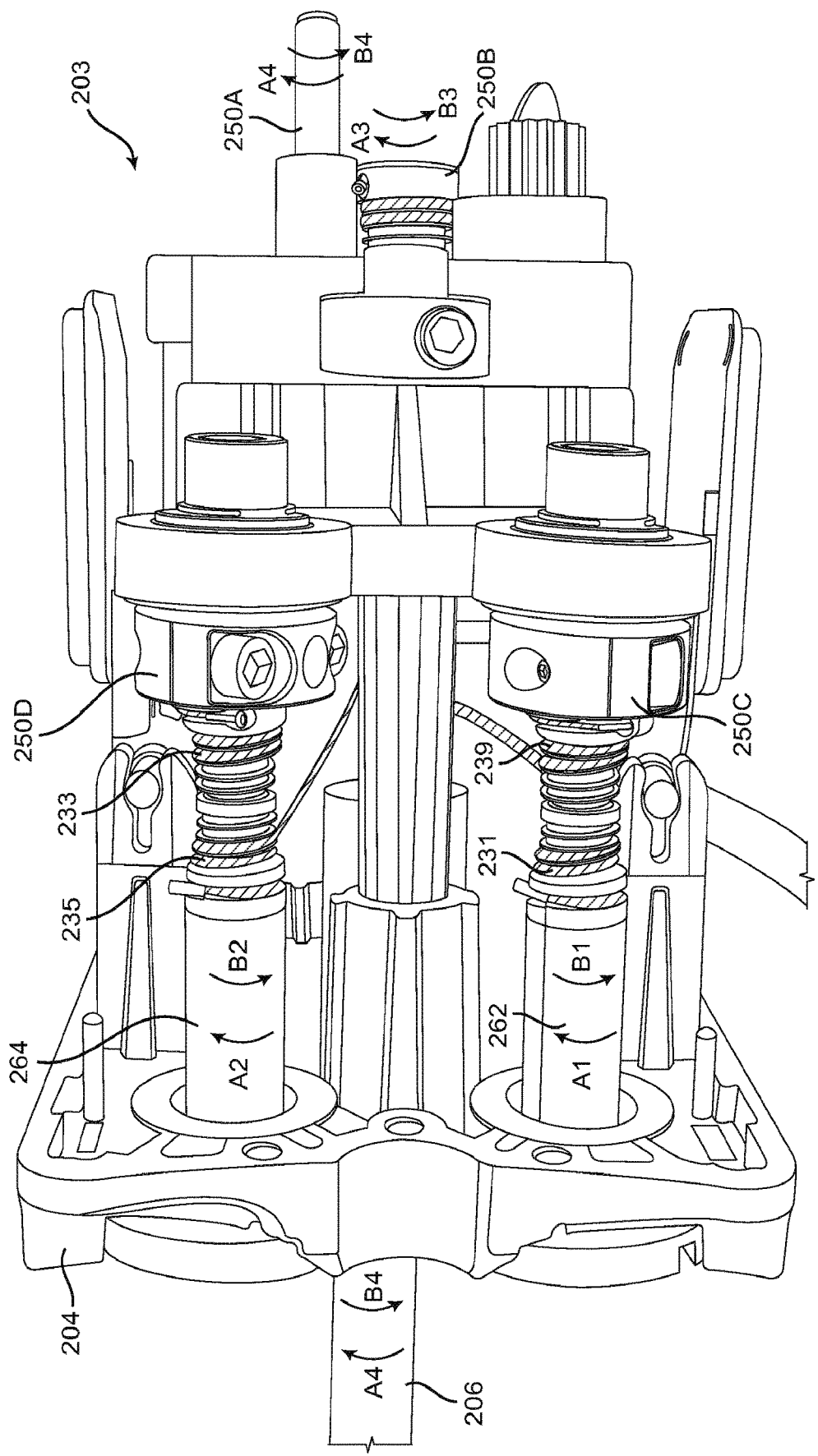

Referring again to FIG. 4, apparatus 200 also includes a plurality of cords or twisted flexible wires 231, 233, 235, 239 and corresponding tubes or rigid linear members 237A-D. Tubes 237A-D are slidably disposed through shaft 206, such that, tubes 237A-D are disposed exterior to tube 272 (i.e., between the exterior of tube 272 and an inner wall of shaft 206). In one embodiment, the distal ends of each of wires 231, 233, 235, 239 are partially disposed through the proximal end of shaft 206 and fixedly coupled to a proximal end 241 of a respective pulling tube 237. For example, the distal end of wire 231 is coupled to the proximal end 241A of tube 237A, the distal end of wire 233 is coupled to the proximal end 241B of tube 237B, the distal end of wire 235 is coupled to the proximal end 241C of tube 237C, and the distal end of wire 239 is coupled to the proximal end 241D of tube 237D. In one embodiment, the proximal ends 241A-D of tubes 237A-D, respectively, are crimped, such that the distal ends of each of wires 231, 233, 235, 239 are fixedly coupled to the proximal ends of tubes 237A, B, C, and D, respectively. In another embodiment, each wire 231, 233, 235, 239 and its respective tube 237 is configured from a single material. A proximal end of each of wires 231, 233, 235, 239 are coupled to actuator 250C or actuator 250D (shown in FIG. 3E and described below). For example, referring to FIG. 3E, actuators 250C and 250D of assembly 203 are shown in accordance with the present disclosure. Actuator 250C includes tubular member 262, where the proximal ends of wires 231 and 239 are wrapped around tubular member 262, as will be described below. Actuator 250D includes tubular member 264, where the proximal ends of wires 233 and 235 are wrapped around tubular member 264, as will be described in greater detail below. As indicated in FIG. 3E, tubular member 262 is configured to rotate in a direction A1 or in an opposite direction B1 and tubular member 264 is configured to rotate in a direction A2 or an opposite direction B2 in response to each of actuators 250C and 250D being rotated by a motor.

The proximal end of wire 231 is wrapped around tubular member 262 in a first direction (e.g., direction A1) and the proximal end of wire 239 is wrapped around tubular member 262 in a second direction (e.g., direction B1) being opposite to the first direction. In one embodiment, a portion of tubular member 262 includes a pair of threads that are embedded around tubular member 262 in a spiraling manner in opposite directions relative to each other. The pair of threads are each configured to receive the proximal ends of wires 231, 239 to be coupled to and wrapped around tubular member 262 in opposite directions.

In this way, when tubular member 262 is rotated in the first direction A1, wire 231 is rotated about tubular member 262, such that, an additional amount of wire 231 is wrapped around tubular member 262 thus pulling wire 231 and tube 237A within tube 272 in a proximal direction toward assembly 203. As tubular member 262 is rotated in direction A1, wire 239 is unwrapped from tubular member 262 causing tension to be released from wire 239 and allowing wire 239 and tube 237D to travel in a distal direction within tube 272. Additionally, when tubular member 262 is rotated in the second direction B1, wire 231 is unwrapped from tubular member 262 causing tension to be released from wire 231 and allowing wire 231 and tube 237A to travel in a distal direction within tube 272. As tubular member 262 is rotated in direction B1, an additional amount of wire 239 is wrapped around tubular member 262, thus pulling wire 239 and tube 237D within tube 272 in a proximal direction toward assembly 203.

The proximal ends of wires 233, 235 are wrapped around tubular member 264. The proximal end of wire 235 is wrapped around tubular member 264 in a first direction (e.g., direction A2) and the proximal end of wire 233 is wrapped around tubular member 264 in a second direction (e.g., direction B2) being opposite to the first direction. In one embodiment, a portion of tubular member 264 has a pair of threads that are embedded around tubular member 264 in a spiraling manner in opposite directions relative to each other. The pair of threads are each configured to receive the proximal ends of wires 233, 235 to be coupled to and wrapped around tubular member 264 in opposite directions.

In this way, when tubular member 264 is rotated in the first direction A2, wire 235 is rotated about tubular member 264, such that, an additional amount of wire 235 is wrapped around tubular member 264 thus pulling wire 235 and tube 237C within tube 272 in a proximal direction toward assembly 203. As tubular member 264 is rotated in direction A2, wire 233 is unwrapped from tubular member 264 causing tension to be released from wire 233 and allowing wire 233 and tube 237B to travel in a distal direction within tube 272. Additionally, when tubular member 264 is rotated in the second direction B2, wire 235 is unwrapped from tubular member 264 causing tension to be released from wire 235 and allowing wire 235 and tube 237C to travel in a distal direction within tube 272. As tubular member 264 is rotated in direction B2, an additional amount of wire 233 is wrapped around tubular member 264, thus pulling wire 233 and tube 237B within tube 272 in a proximal direction toward assembly 203.

In one embodiment, assembly 203 also includes a flexible twisted wire 253, shown in FIG. 3D. One end of flexible twisted wire 253 is wrapped around actuator 250B and the other end of wire 253 is coupled to interfacing block 256. When actuator 250B is rotated (e.g., via a motor, as described above) in a first direction (e.g., direction A3), cable 253 unwraps from actuator 250B and tension is released from wire 253. In one embodiment, interfacing block 256 is biased toward sealing block 260 (e.g., via a spring). In this way, when tension is released from wire 253 (i.e., via rotating actuator 250B in a first direction A3), interfacing block 256 is biased in a distal direction toward block 260, causing wire 270 to be advanced in a distal direction (i.e., toward tip 208) within tube 272. When actuator 250B is rotated in a second direction (e.g., direction B3), an additional amount of wire 253 is wrapped around actuator 250B, causing wire 253 to pull interfacing block 256 in a proximal direction away from block 260, which also causes wire 270 to be retracted in a proximal direction (i.e., away from tip 208) within tube 272.

Alternatively, in another embodiment, the proximal and distal motion of block 256 may be controlled solely by actuator 250B and wire 253 without requiring block 256 to be biased toward sealing block 260. In this embodiment, each end of flexible twisted wire 253 may be wrapped around actuator 250B in an opposite direction (i.e., one end is wrapped around actuator 250B in direction A3 and the other end is wrapped around actuator 250B in a direction B3). A central portion of wire 253 is coupled to interfacing block 256 and a constant tension is maintained in wire 253. When actuator 250B is rotated in a first direction (e.g., A3), a first end of wire 253 is further wrapped around actuator 250B and a second end of wire 253 is unwrapped from around actuator 250B, causing block 256 to slide in a distal direction and causing wire 270 to extend in a distal direction. When actuator 250B is rotated in a second direction (e.g., B3), the first end of wire 253 is unwrapped from around actuator 250B and the second end of wire 256 is further wrapped around actuator 250B, causing block 253 to slide in a proximal direction and causing wire 270 to retract in a proximal direction.

In one embodiment, actuator 250A is coupled to a proximal end of shaft 206, such that, when actuator 250A is rotated, shaft 206 is rotated in an opposite direction. In this embodiment, when actuator 250A is rotated in a direction A4, shaft 206 is rotated in a direction B4. Alternatively, when actuator 250A is rotated in an opposite direction B4, shaft 206 is rotated in the opposite direction A4. As described below, a distal portion of shaft 206 is coupled to tip 208. In this way, actuator 250A may be rotated to rotate tip 208. It is to be appreciated that, in one embodiment, tube 272 is configured to have sufficient flexibility to be twisted within shaft 206 to enable the rotation of shaft 206.

Figure 5A:
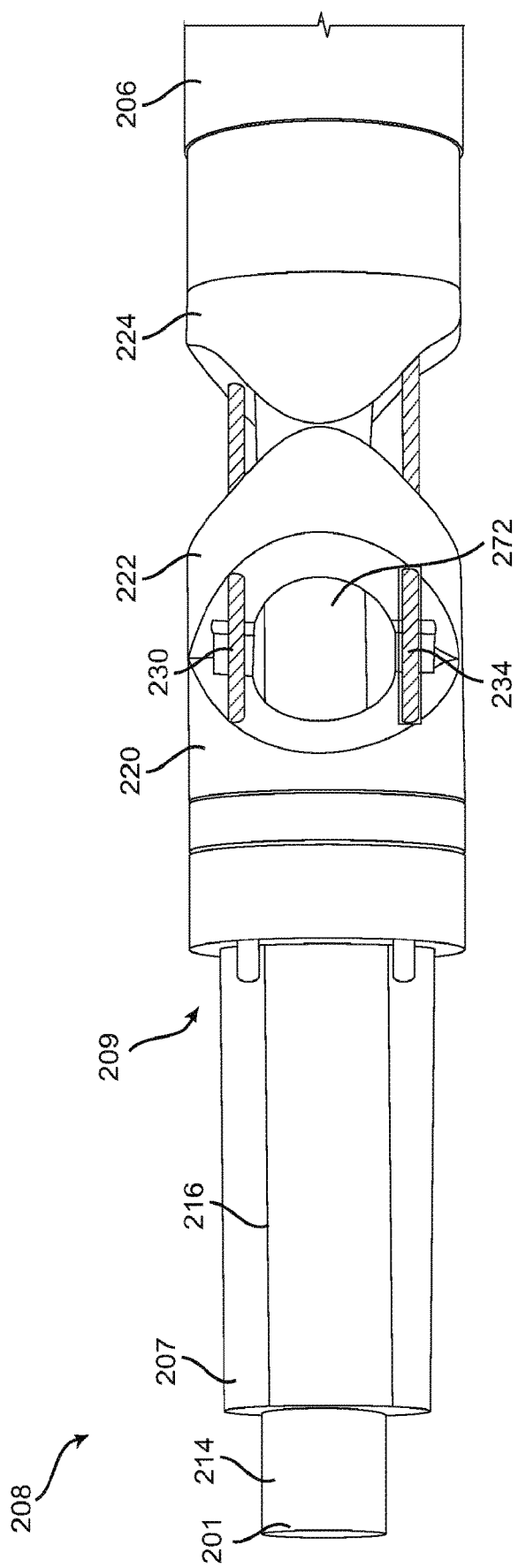
FIG. 5A is a side view of the robotic tip of the electrosurgical apparatus of FIG. 2 in accordance with an embodiment of the present disclosure.
Figure 5B:
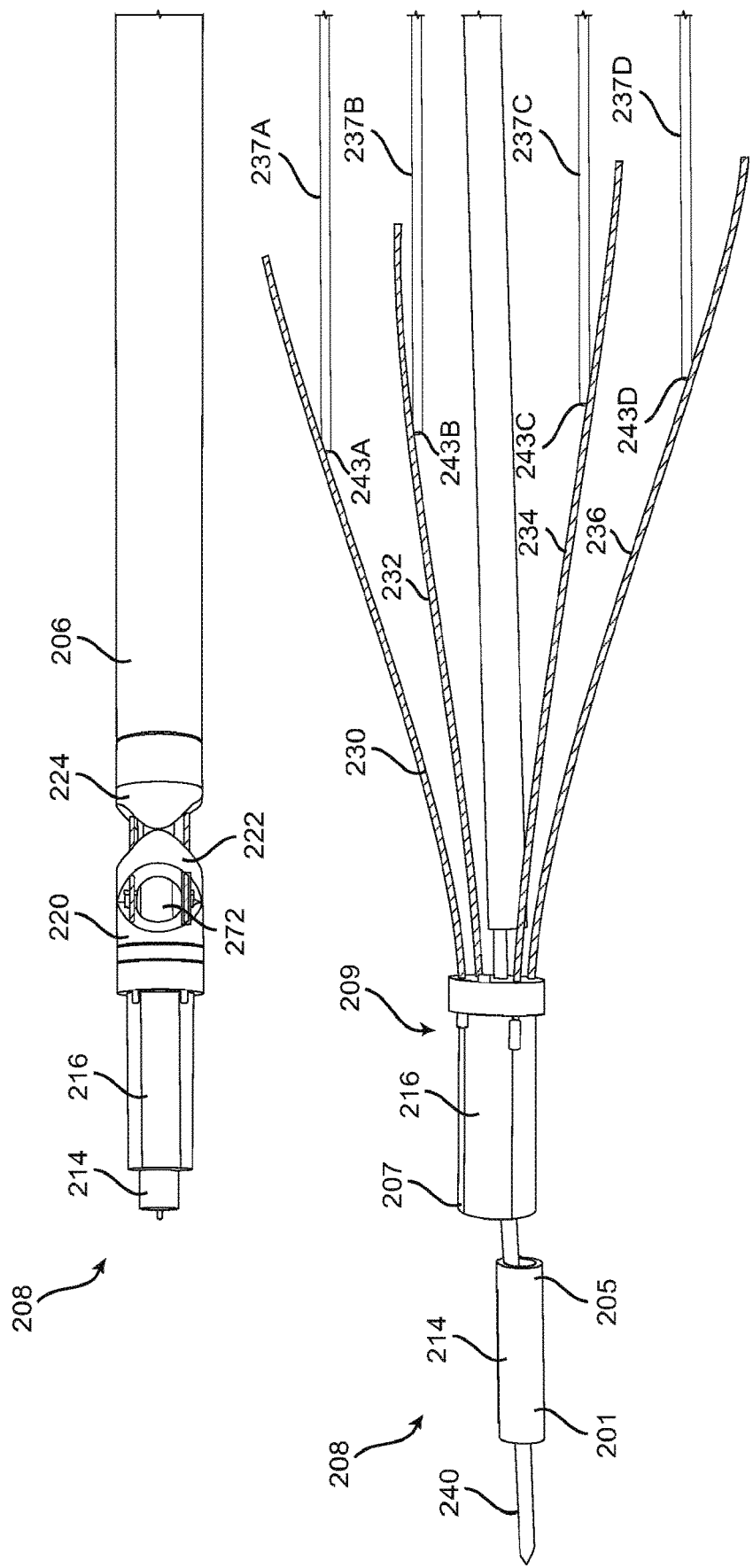
FIGS. 5B and 5C are partial exploded views of the robotic tip of the electrosurgical apparatus of FIG. 2 in accordance with an embodiment of the present disclosure.
Figure 5C:
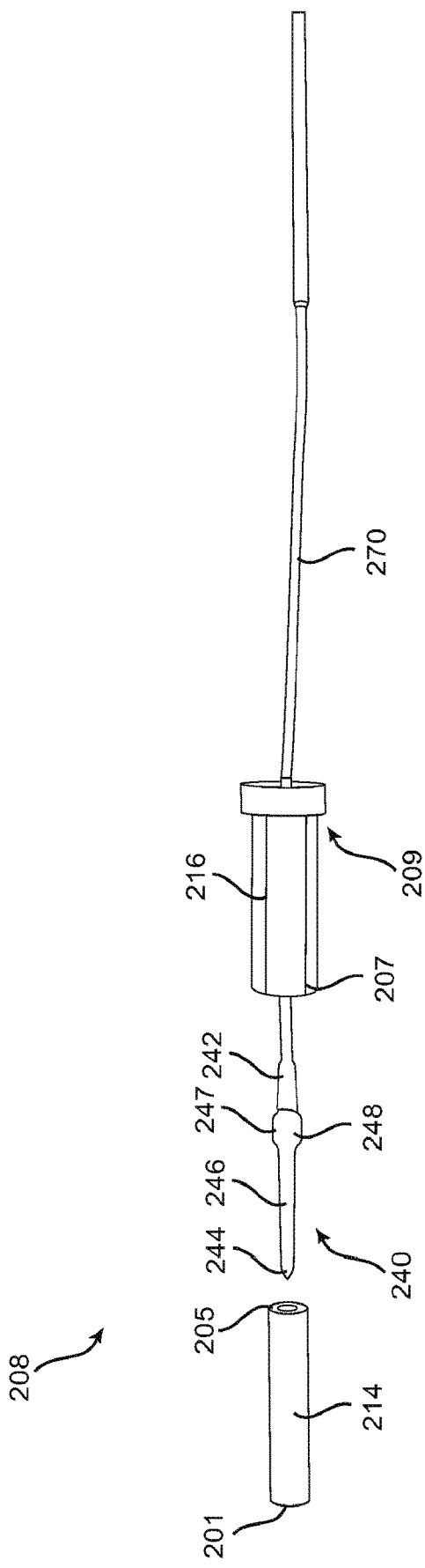

Referring to FIGS. 5A, 5B, and 5C, a side view of robotic tip 208 is shown in FIG. 5A and side exploded views of tip 208 are shown in FIGS. 5B and 5C in accordance with the present disclosure. Robotic tip 208 includes electrode 240, ceramic insert 214, tip holder 216, and hinging members 220, 222, and 224. Ceramic insert 214 and tip holder 216 are each configured in a generally cylindrical shape. Ceramic insert 214 includes a distal end 201 and a proximal end 205 and a channel extending from end 201 to end 205 through the interior of insert 214. Tip holder 216 includes a distal end 207 and a proximal end 209 and a channel extending from end 207 to end 209 through the interior of holder 216. As shown in FIG. 5A, proximal end 205 of ceramic insert 214 is disposed into and fixedly coupled to the distal end 207 of holder 216. It is to be appreciated that the ceramic insert 214 and tip holder 216 together form an electrode housing, with the distal end 201 of ceramic insert 214 being the distal end of the electrode housing and the proximal end 209 of tip holder 216 being the proximal end of the housing. Proximal end 209 of tip holder 216 is disposed over the distal end of tube 272. Although not shown, a rubber gasket is disposed around the distal end of tube 272 within holder 216. The rubber gasket forms a seal around the distal end of tube 272 to prevent leakage of the inert gas at the tip 208.

Figure 6A:
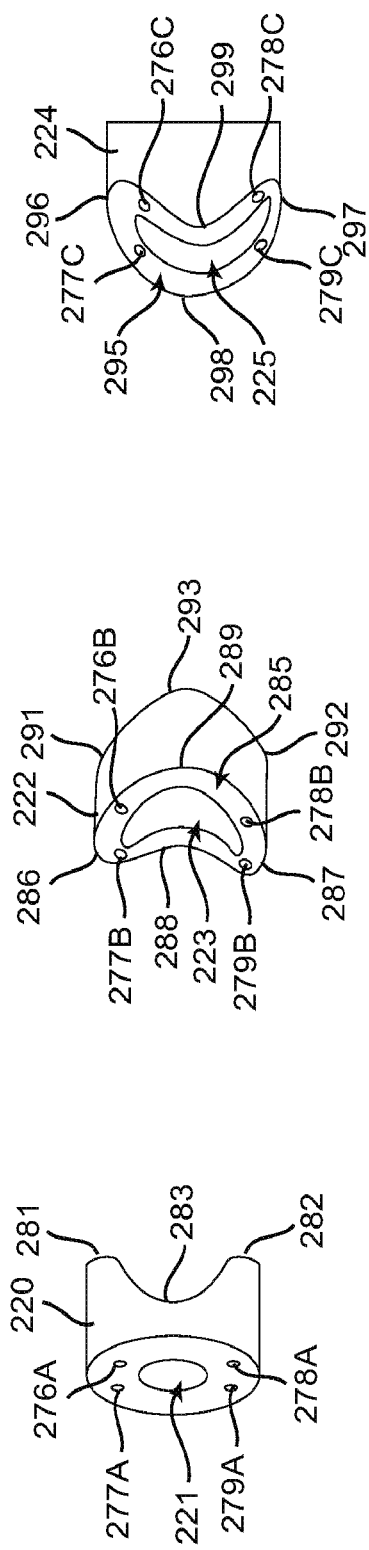
FIGS. 6A and 6B are views of hinging members of the robotic tip of the electrosurgical apparatus of FIG. 2 in accordance with an embodiment of the present disclosure.
Figure 6B:
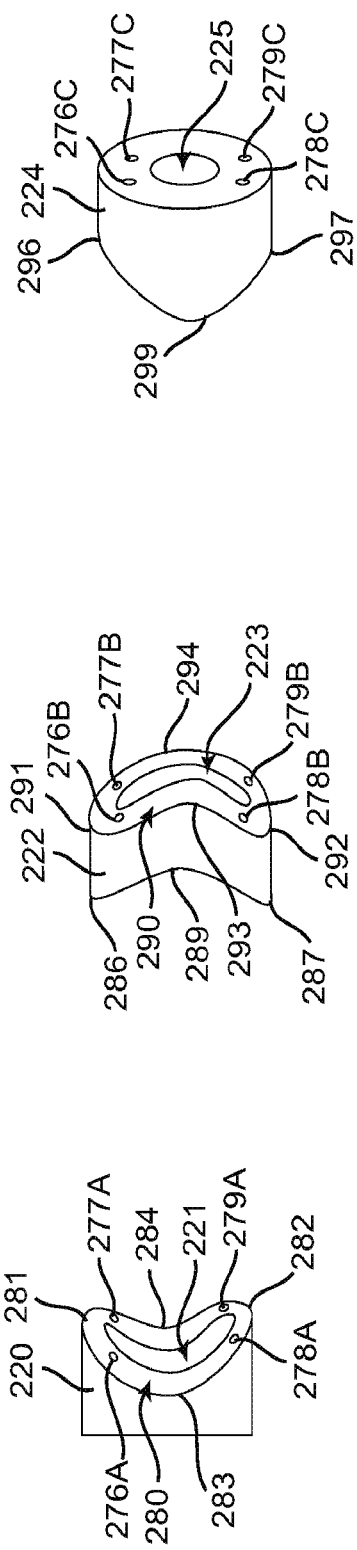

A distal end of shaft 206 is coupled to hinging member 224, such that, a distal end of tube 272 is disposed through apertures 221, 223, 225 of hinging members 220, 222, 224 (FIGS. 6A and 6B further illustrate apertures of hinging members 220, 222, 224). The distal end of tube 272 is coupled to proximal end 209 of tip holder 216. A distal end of wire 270 is disposed through the distal end of tube 272, the holder 216, and ceramic insert 214. As shown in FIG. 5C, the distal end of wire 270 is coupled to an electrode 240, where electrode 240 is slidably disposed through the inner channel of ceramic insert 214.

In one embodiment, electrode 240 is configured as a conducting blade. As shown in FIG. 5C, electrode 240 includes a distal end 244 and a proximal end 242. The distal end of wire 270 is coupled to the proximal end 242 of electrode 240. Electrode 240 also includes extension members 247, 248 and a blade portion 246, which extends distally from extension members 247, 248 to distal end 244 of electrode 240. It is to be appreciated that blade portion 246 is configured with sharp cutting edges that are suitable for mechanical cutting (i.e., excising tissue with no RF energy being applied to the blade portion similar to using a scalpel or the like). Although, electrode 240 is shown and described as a conducting blade, it is to be appreciated that in other embodiments electrode 240 may be configured as a conducting needle or any other type of shape suitable for use as a conducting electrode in surgical applications.

Figure 5D:
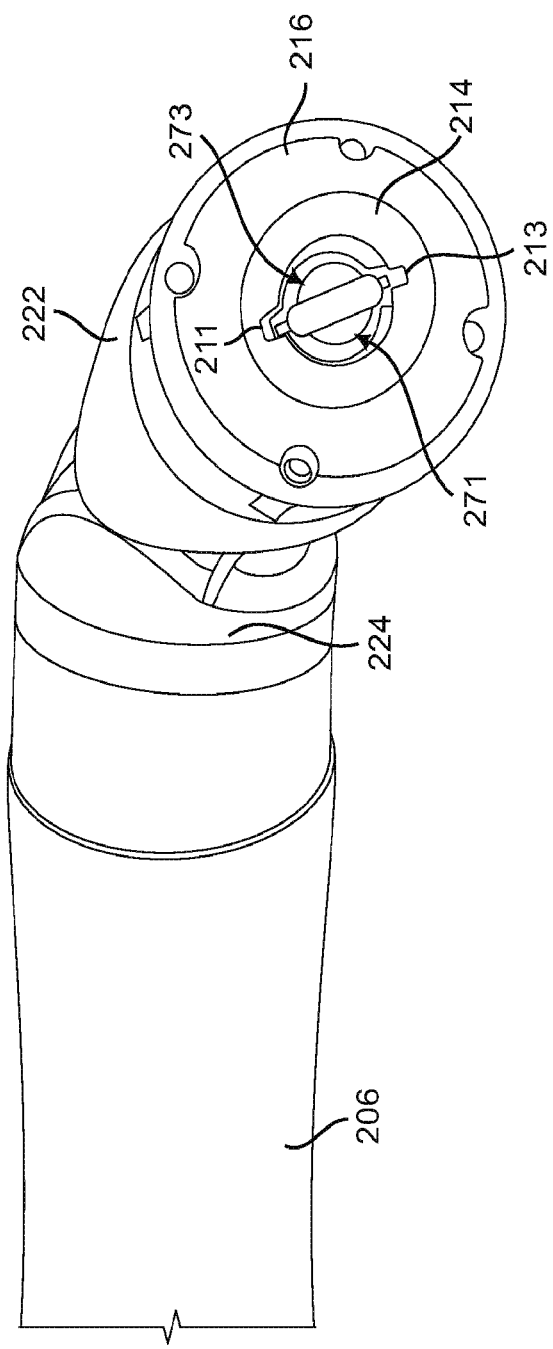
FIG. 5D is a perspective view of the robotic tip of the electrosurgical apparatus of FIG. 2 in accordance with an embodiment of the present disclosure.

Referring to FIG. 5D, in one embodiment, ceramic insert 214 includes a pair of diametrically opposed slots 211 and 213 disposed in the inner wall of the channel of insert 214. Extension members 247, 248 of electrode 240 are slidably disposed within slots 211, 213, respectively, such that electrode 240 is slidable with respect to ceramic insert 214. In this way, when actuator 250B is rotated in a first direction or a second opposite direction to slidably extend or retract interfacing block 256, wire 270 is also extended or retracted within tube 272 causing electrode 240 to be extended or retracted. It is to be appreciated that, since ceramic insert 214 is fixedly coupled to tip holder 216 such that electrode 240 and ceramic insert are fixed rotationally with respect to tip holder 216.

Figure 5H:
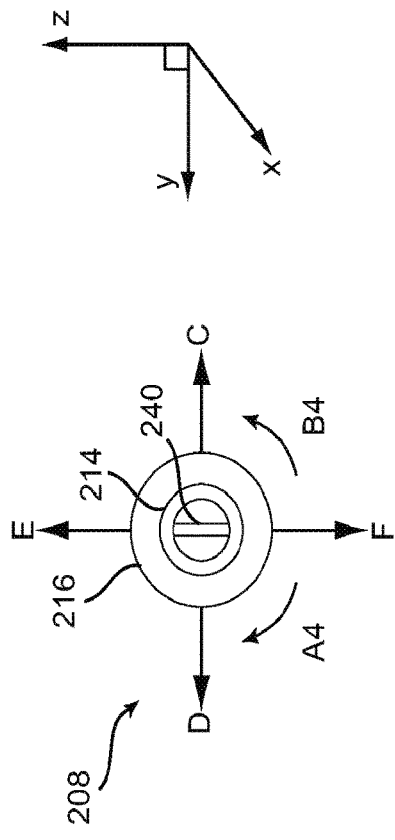
FIG. 5H is a view through the distal end of the robotic tip of the electrosurgical apparatus of FIG. 2 in accordance with an embodiment of the present disclosure.
Figure 5E:
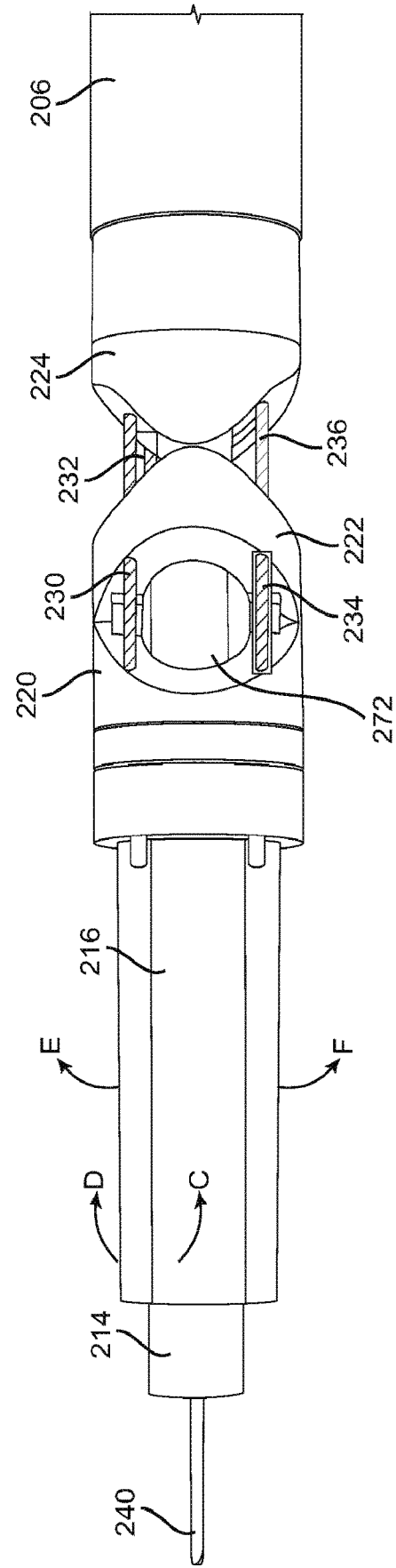
FIG. 5E is a side view of the robotic tip of the electrosurgical apparatus of FIG. 2 with an electrode in an extended position in accordance with an embodiment of the present disclosure.

Referring to FIG. 5E, electrode 240 is shown in an advanced or extended position in accordance with the present disclosure. As shown in FIG. 5E, when electrode 240 is extended (by rotating actuator 250B), the distal end 244 of electrode 240 extends passed the distal end 201 of insert 214 until the blade portion 246 is disposed passed distal end 201 of insert 214.

As shown in FIG. 5B, apparatus 200 includes flexible wires 230, 232, 234, and 236. The distal ends of each of wires 230, 232, 234, 236 are fixedly coupled to the proximal end 209 of holder 216. The proximal ends of wires 230, 232, 234, 236 are each partially-disposed through the distal end of shaft 206 and fixedly coupled to the distal ends 243 of tubes 237, where the proximal end of wire 230 is coupled to distal end 243A of tube 237A, the proximal end of wire 232 is coupled to distal end 243B of tube 237B, the proximal end of wire 234 is coupled to distal end 243C of tube 237C, and the proximal end of wire 236 is coupled to distal end 243D of tube 237D. In one embodiment, each of distal ends 243 are crimped, such that the proximal ends of wires 230, 232, 234, 236 are fixedly coupled to distal ends 243. It is to be appreciated that in certain embodiments, wires 230, 232, 234, 235, respective tubes 237 and respective wires 231, 233, 235, 239 are configured from a single material and are of unitary constructions. For example, wire 230, respective tube 237A and wire 231 may be a single wire or component as opposed to three separate components as shown.

As stated above, tubes 237 are configured as rigid tubes and slidably disposed within shaft 206. Tubes 237 are configured to transfer the pushing and pulling (i.e., the creation and release of tension) of wires 231, 233, 235, 239 responsive to the rotation of actuators 250C and 250D to wires 230, 232, 234, and 236. In this way, apparatus 200 includes 4 pulling mechanisms comprising one tube and two wires: (1) wires 230, 231, and tube 237A; (2) wires 232, 233, and tube 237B; (3) wires 234, 235, and tube 237C; and (4) wires 236, 239, and tube 237D. For example, when tubular member 262 of actuator 250C is rotated in a direction A1 (shown in FIG. 3E), tension is created in wire 234 and tension is released in wire 232. Alternatively, when tubular member 262 of actuator 250C is rotated in a direction B1, tension is released in wire 234 and tension is created in wire 232. When tubular member 264 of actuator 250D is rotated in a direction A2 (shown in FIG. 3E), tension is created in wire 230 and tension is released in wire 236. Alternatively, when tubular member 264 of actuator 250D is rotated in a direction B2, tension is released in wire 230 and tension is created in wire 236.

Each pulling mechanism is configured to transfer the pushing and pulling of wires 231, 233, 235, 239 (created in response to the rotation of actuators 250C and 250D) to a hinging mechanism of tip 208. Referring again to FIG. 5A, the hinging mechanism includes hinging members 220, 222, 224. Hinging members 220, 222, 224 are included in robotic tip 208 to enable tip 208 to be pivoted and rotated relative to shaft 206 in a variety of ways. Referring to FIGS. 6A and 6B, exploded views of hinging members 220, 222, 224 are shown in accordance with the present disclosure. Hinging members 220, 222, 224 are each configured in a generally cylindrical shape. Hinging member 220 includes apertures, 221, 276A, 277A, 278A, and 279A and a curved surface 280 having protruding or convex portions 281, 282 and recessed concave portions 283, 284, where protruding portions 281, 282 are diametrically opposed about surface 280 and recessed portions 283, 284 are diametrically opposed about surface 280. Hinging member 222 includes apertures, 223, 276B, 277B, 278B, and 279B and a curved surface 285 having protruding or convex portions 286, 287 and recessed or concave portions 288, 289, where protruding portions 286, 287 are diametrically opposed about surface 285 and recessed portions 288, 289 are diametrically opposed about surface 285. Hinging member 222 also includes a curved surface 290 having recessed or concave portions 291, 292 and protruding or convex portions 293, 294, where recessed portions 291, 292 are diametrically opposed about surface 290 and protruding portions 293, 294 are diametrically opposed about surface 290. Hinging member 224 includes apertures, 225, 276C, 277C, 278C, and 279C and a curved surface 295 having recessed or concave portions 296, 297 and protruding or convex portions 298, 299, where recessed portions 296, 297 are diametrically opposed about surface 295 and protruding portions 298, 299 are diametrically opposed about surface 295.

Hinging member 220 is hingedly coupled to hinging member 222, such that, protruding portion 281 of surface 280 is hingedly coupled to protruding portion 286 and protruding portion 282 of surface 280 is hingedly coupled to protruding portion 287. In this way, hinging member 220 may be pivoted about hinging member 222 until recessed portion 283 of surface 280 comes into contact with recessed portion 289 of surface 285. Alternatively, hinging member 220 may be pivoted about hinging member 222 until recessed portion 284 of surface 280 comes into contact with recessed portion 288 of surface 285.

Hinging member 222 is hingedly coupled to hinging member 224, such that, protruding portion 293 of surface 290 is hingedly coupled to protruding portion 299 of surface 295 and protruding portion 294 of surface 290 is hingedly coupled to protruding portion 298 of surface 295. In this way, hinging member 222 may be pivoted about hinging member 224 until recessed portion 291 of surface 290 comes into contact with recessed portion 296 of surface 295. Alternatively, hinging member 222 may be pivoted about hinging member 224 until recessed portion 292 of surface 290 comes into contact with recessed portion 297 of surface 295.

Referring to FIGS. 5A, 5B, 5E, 6A, and 6B, hinging member 224 is coupled to a distal end of shaft 206 and hinging member 220 is coupled to proximal end 209 of holder 216. The distal end of wire 230 is disposed through apertures 276A, 276B, 276C of hinging members 220, 222, 224, respectively, and fixedly coupled to proximal end 209 of holder 216. The distal end of wire 232 is disposed through apertures 277A, 277B, 277C of hinging members 220, 222, 224, respectively, and fixedly coupled to proximal end 209 of holder 216. The distal end of wire 234 is disposed through apertures 278A, 278B, 278C of hinging members 220, 222, 224, respectively, and fixedly coupled to proximal end 209 of holder 216. The distal end of wire 236 is disposed through apertures 279A, 279B, 279C of hinging members 220, 222, 224, respectively, and fixedly coupled to proximal end 209 of holder 216.

As best seen in FIGS. 5A and 5E, when hinging members 220, 222, 224 are coupled together, the distal end of tube 272 is disposed through apertures 221, 223, and 225 and coupled to the distal end 209 of holder 216.

As stated above, actuators 250C and 250D may be rotated (in directions A1/A2 or B1/B2, shown in FIG. 3E) to pull or create tension in wires 230, 232, 234, 236 or release tension in wires 230, 232, 234, 236. The design of hinging members 220, 222, 224 is configured to take advantage of this ability to pivot tip holder 216 (and thus electrode 240) in a plurality of ways. As will be described in greater detail below, hinging members 222, 224 enable holder 216 to be pivoted relative to shaft 206 along a first two-dimensional plane responsive to the selective pulling of one or more of wires 230, 232, 234, 236. Referring to FIG. 5E, the first two-dimensional plane is indicated by the x-y plane, where the y-axis corresponds to the longitudinal axis along which shaft 206 is disposed on and the x-axis traverses the y-axis. Furthermore, hinging members 220, 222 enable holder 216 to be pivoted relative to shaft 206 along a second two-dimensional plane responsive to the selective pulling of one or more of wires 230, 232, 234, 236. The second two-dimensional plane is indicated by the y-z plane in FIG. 5E, where the z-axis traverses the y-axis. In combination, hinging members 220, 222, 224 enable three-dimensional pivoting of holder 216 to shaft 206.

Figure 5F:
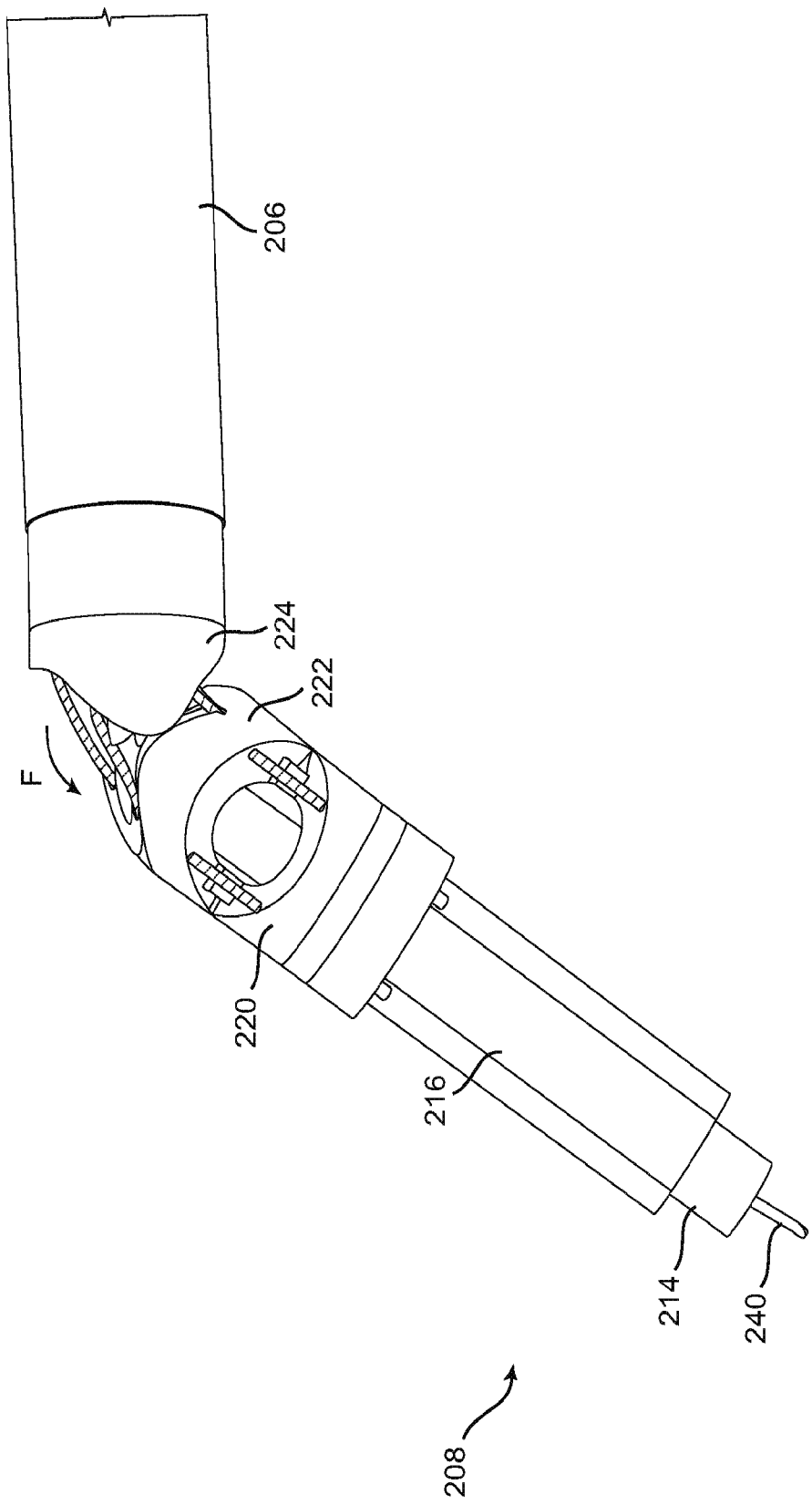
FIGS. 5F and 5G are views of the robotic tip of the electrosurgical apparatus of FIG. 2 while pivoted in accordance with an embodiment of the present disclosure.

For example, referring to FIGS. 3E, 5E, 6A, 6B, when tubular member 262 is rotated in direction A1 and tubular member 264 is rotated in a direction B2, tension is created in wires 230 and 232 and tension is released in wires 234 and 236 to pivot hinging member 222 about hinging member 224, such that, recessed portion 291 of surface 290 is drawn toward recessed portion 296 of surface 295 to pivot holder 216 in a direction E along the y-z plane (indicated in FIG. 5E). When tubular member 262 is rotated in a direction B1 and tubular member 264 is rotated in a direction A2, tension is created in wires 234 and 236 and tension is released in wires 230 and 232 to pivot hinging member 222 about hinging member 224, such that, recessed portion 292 of surface 290 is drawn toward recessed portion 297 of surface 295 to pivot holder 216 in a direction F along the y-z plane (indicated in FIG. 5E), where direction F is opposite to direction E. Referring to FIG. 5F, robotic tip 208 is shown with tip holder 216 pivoted in a direction F in accordance with the present disclosure.

When tubular member 262 and 264 are each rotated in directions A1, A2, respectively, tension is created in wires 230 and 234 and tension is released in wires 232 and 236 to pivot hinging member 220 about hinging member 222, such that, recessed portion 283 of surface 280 is drawn toward recessed portion 289 of surface 285 to pivot holder 216 in a direction C along the y-x plane (i.e., a direction perpendicular to directions E and F). When tubular members 262 and 264 are each rotated in opposite directions B1, B2, respectively, tension is created in wires 232 and 236 and tension is released in wires 230 and 234 to pivot hinging member 220 about hinging member 222, such that, recessed portion 284 of surface 280 is drawn toward recessed portion 289 of surface 285 to pivot holder 216 in a direction D along the y-x plane (i.e., perpendicular to directions E and F), where direction D is opposite to direction C.

It is to be appreciated that different combinations of wires 230, 232, 234, 236 may be pulled or released by actuators 250C and 250D to pivot holder 216 three-dimensionally in directions between directions C, D, E, and F creating a hemi-sphere of possible orientations for holder 216 (and thus electrode 240) relative to shaft 206 using the design of robotic tip 208.

Figure 5G:
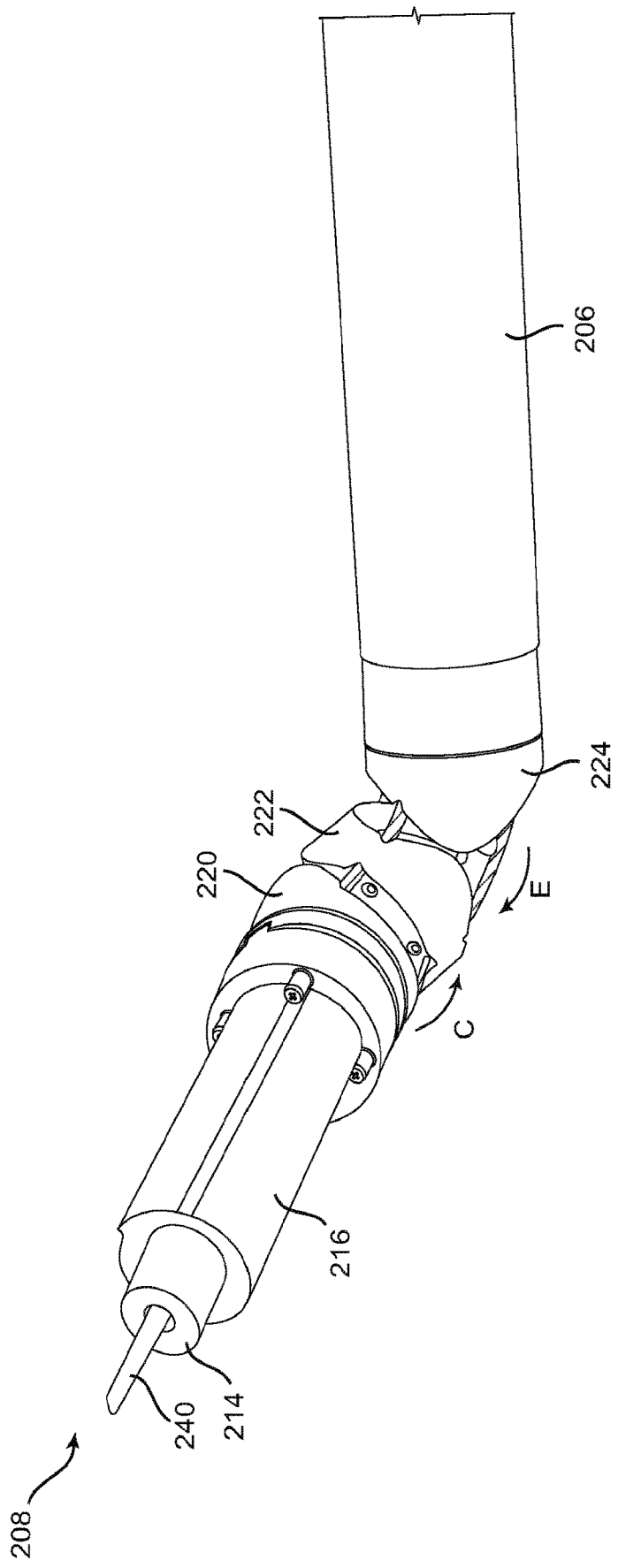

To pivot holder 216 in directions between C, D, E, and F, as shown in FIGS. 5E and 5H, one of tubular members 262/264 may be rotated in a direction A/B, while the other tubular member 262/264 is either maintained stationary (or rotated fewer revolutions) relative to the first tubular member 262/264. For example, if tubular member 262 is rotated in a direction A1, while tubular member 264 is maintained in a stationary position (or rotated slightly in direction B2), tension is created in wire 230 and released in wire 236, such that, wire 230 has more tension than wires 232, 234, and 236, and wire 236 has less tension than wires 230, 232, 234 The resulting tensions pivot holder 216 in a direction between directions E and C. Referring to FIG. 5G, robotic tip 208 is shown with tip holder 216 pivoted in a direction between directions C and E. It is to be appreciated that actuators 250C and 250D may be used to control and vary the tension in any one of the wires 230, 232, 234, 236 in many different ways to effectuate many different orientations for holder 216 relative to shaft 206.

To maintain a "zero rotation" position for robotic tip 208 (i.e., where tip 208 is straight, such that, shaft 206 and tip 208 are collinear as shown in FIGS. 5A and 5E), tubular members 262, 264 are maintained in a static position, such that, equal tension is maintained in all of wires 230, 232, 234, 236 and no resulting force is applied to tip 208 in direction C, D, E, F. When tip 208 is pivoted about one or more of hinging members 220, 222, 224 in directions C, D, E, and/or F, to return tip 208 to a "zero rotation" or neutral position, tubular members 262, 264 are appropriately rotated until an equal amount of tension is reached in each of wires 230, 232, 234, 236.

As stated above, actuator 250A may be rotated (in directions A4 or B4, shown in FIG. 3E) to rotate shaft 206. When actuator 250A is rotated in a first direction (e.g., direction A4), shaft 206 and tip 208 are rotated in an opposite direction (e.g., direction B4, shown in FIG. 5H). When actuator 250A is rotated in a second direction (e.g., direction B4), shaft 206 and tip 208 are rotated in an opposite direction (e.g., direction A4, shown in FIG. 5H). The ability to rotate tip 208 further increases the amount of orientations and positions achievable by tip holder 216 (and thus electrode 240).

It is to be appreciated that electrode 240 is configured in a generally planar shape. When electrode 240 is disposed in the inner channel of ceramic insert 214, gas passageways 271, 273 are formed on either side of electrode 240 (shown in FIG. 5D). In this way, when gas is provided from assembly 203, through tube 272, and through the inner channels of tip holder 216 and ceramic insert 214, the gas will pass over electrode 240 and out of the distal end 201 of ceramic tip 201. It is to be appreciated that, as stated above, a rubber sealing gasket is disposed over the distal end of tube 272, such that, the sealing gasket prevents gas provided through tube 272 into the inner channels of holder 216 and insert 214 from escaping the distal end of tube 272 and the proximal end 209 of holder 216 as gas flows.

When electrode 240 is in the retracted position, i.e., disposed within the inner channel of ceramic insert 214, as shown in FIG. 5A, apparatus 200 is suitable for generating plasma. In the retracted position, RF energy is conducted to blade portion 246 of electrode 240 from an electrosurgical generator such, as ESU 12, via cable 210, wire 258 and wire 270. An inert gas, such as helium or argon, is then supplied through the tube 272 from either the electrosurgical generator or an external gas source coupled to tube 272 via cable 210 and gas port 252. As the inert gas flows over the blade portion 246 of the electrode 240 while electrode 240 is held at high voltage and high frequency, a cold plasma beam is generated and emitted from the distal end 201 of ceramic insert 214. The plasma beam may then be used in a desired surgical application.

Referring to FIG. 5E, electrode 240 is shown in an extended or advanced position such that blade portion 246 is extended passed the distal end 201 of ceramic insert 214. It is to be appreciated that, as long as electrode 240 is not in contact with the tissue of a patient, while electrode 240 is in an advanced position, apparatus 200 is also suitable for generating plasma in the manner described above (i.e., by providing inert gas flow over electrode 240, while electrode is held at high voltage and high frequency). Furthermore, while electrode 240 is in an advanced position, apparatus 200 can also be used for two cutting modes: mechanical cutting and electrosurgical cutting. In the mechanical cutting mode, RF or electrosurgical energy is not applied to wire 270 or electrode 240, and therefore, the electrode 240 is in a de-energized state. In this mode, the blade portion 246 of electrode 240 can be used to excise tissue via mechanical cutting, i.e., the blade portion makes physical contact with the tissue. After the tissue is removed, gas may be applied to electrode 240 (while electrode 240 is advanced or retracted) to generate a cold plasma beam for cauterization, sterilization and/or hemostasis of the operative patient site.

In the electrosurgical cutting mode, electrode 240 is advanced and used while both electrically energized and enveloped with inert gas flow. This configuration resembles an electrosurgical knife approach, where the electrosurgical energy does the cutting. However, with the addition of the inert gas flow, cuts made show virtually no eschar, with very little collateral damage along the side walls of the cut. The cutting speed is considerably faster, with less mechanical cutting resistance as compared to when the knife blade is not electrically energized, i.e., the mechanical cutting mode. Hemostasis is also affected during this process.

It is to be appreciated that in either of the electrosurgical cutting or the mechanical cutting modes described above, electrosurgical apparatus 200 is configured to effectuate the cutting motion of electrode 240 (i.e., the translational path of electrode 240 across tissue to treat or otherwise remove tissue) via the rotation of actuators 250A-D in multiple ways. The path of electrode 240 during either of the cutting modes may be controlled via the selective rotation of actuators 250C and 250D to pivot tip 208 relative to shaft 206 as desired. The path of electrode 240 may further be controlled via the selective rotation of actuator 250A to rotate shaft 206 and tip 208 about the longitudinal axis. For example, where tip 208 is pivoted relative to shaft 206, the rotation of shaft 206 about the longitudinal axis causes tip 208 (and thus the extended electrode 240) to move in a circular motion. Rotation of shaft 206 and tip 208 also serves as a means to choose the orientation of the sharp edges of electrode 240 to enable cutting at varying angles across tissue. The path of electrode 240 may further be controlled by changing the length electrode 240 extends past distal end 201 of ceramic insert 214 via the selective rotation of actuator 250B. By altering the length electrode 240 extends past distal end 201, the length and depth of cuts or incisions to patient tissue can be selected with high precision as desired. The length electrode 240 extends past distal end 201 may also be oscillated or varied in time (by alternating the directions A3 and B3 that actuator 250B is rotated in) to create a sawing or puncturing motion of electrode 240. The sawing or puncturing motion may be implemented in the mechanical cutting mode to aid in cutting tissue.

As stated above, in an alternative embodiment, blocks 256 and 260 may be configured as a single component. For example, referring to FIGS. 7A, 7B, 7C, apparatus 200 is shown with a block or sliding member 350 instead of blocks 256, 260 in accordance with the present disclosure. Block 350 includes ends 351, 352, and tube receiving members 356, 358, where tube receiving member 358 extends from a surface 354 of block 350. Block 350 is slidably mounted to brackets 251A, 251B, where end 351 is slidably mounted to bracket 251A and end 352 is slidably mounted to bracket 251B.

Figure 7A:
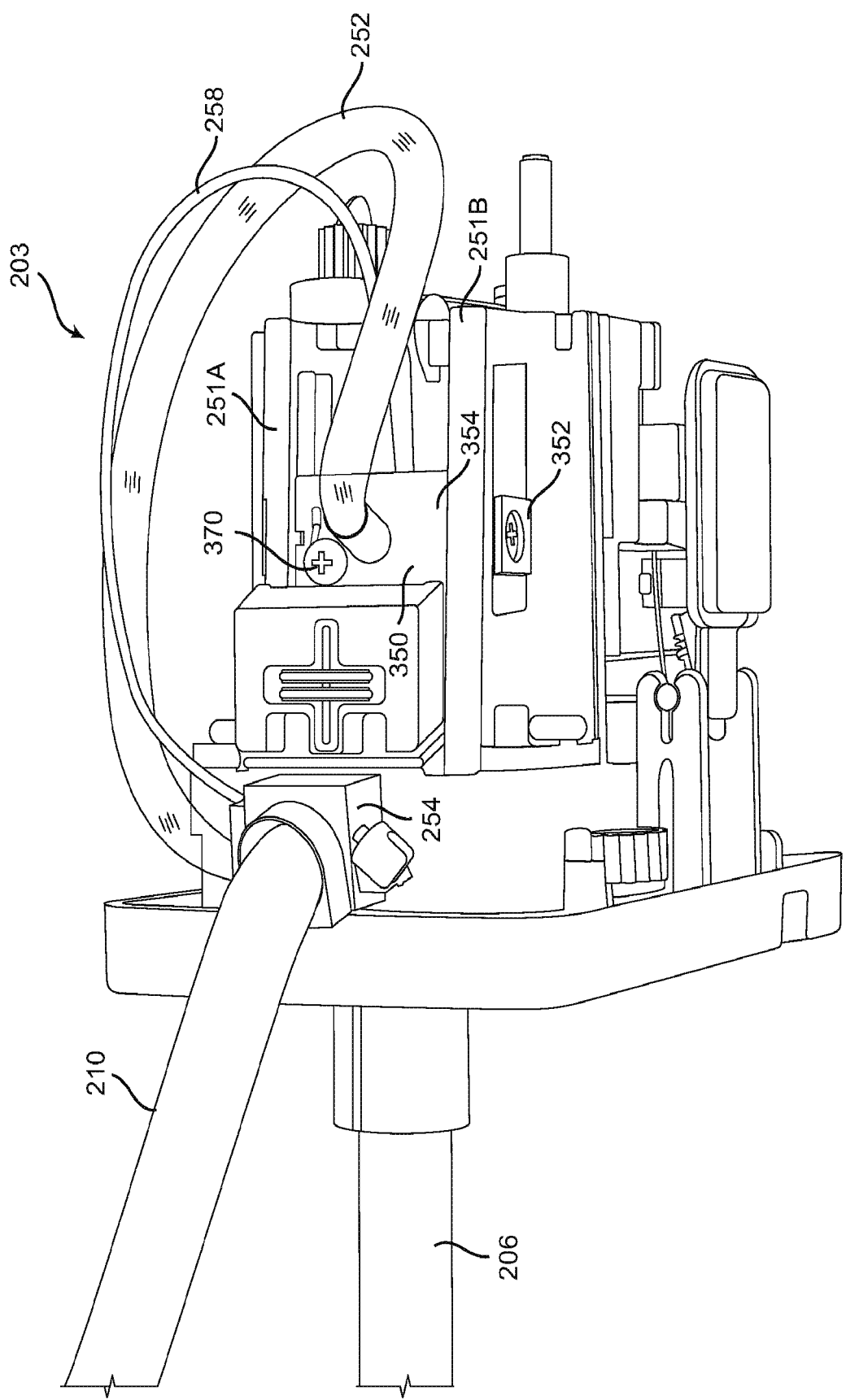
FIGS. 7A-7C are perspective views of the assembly of FIG. 3A including an alternative sliding block in accordance with an embodiment of the present disclosure.
Figure 7B:
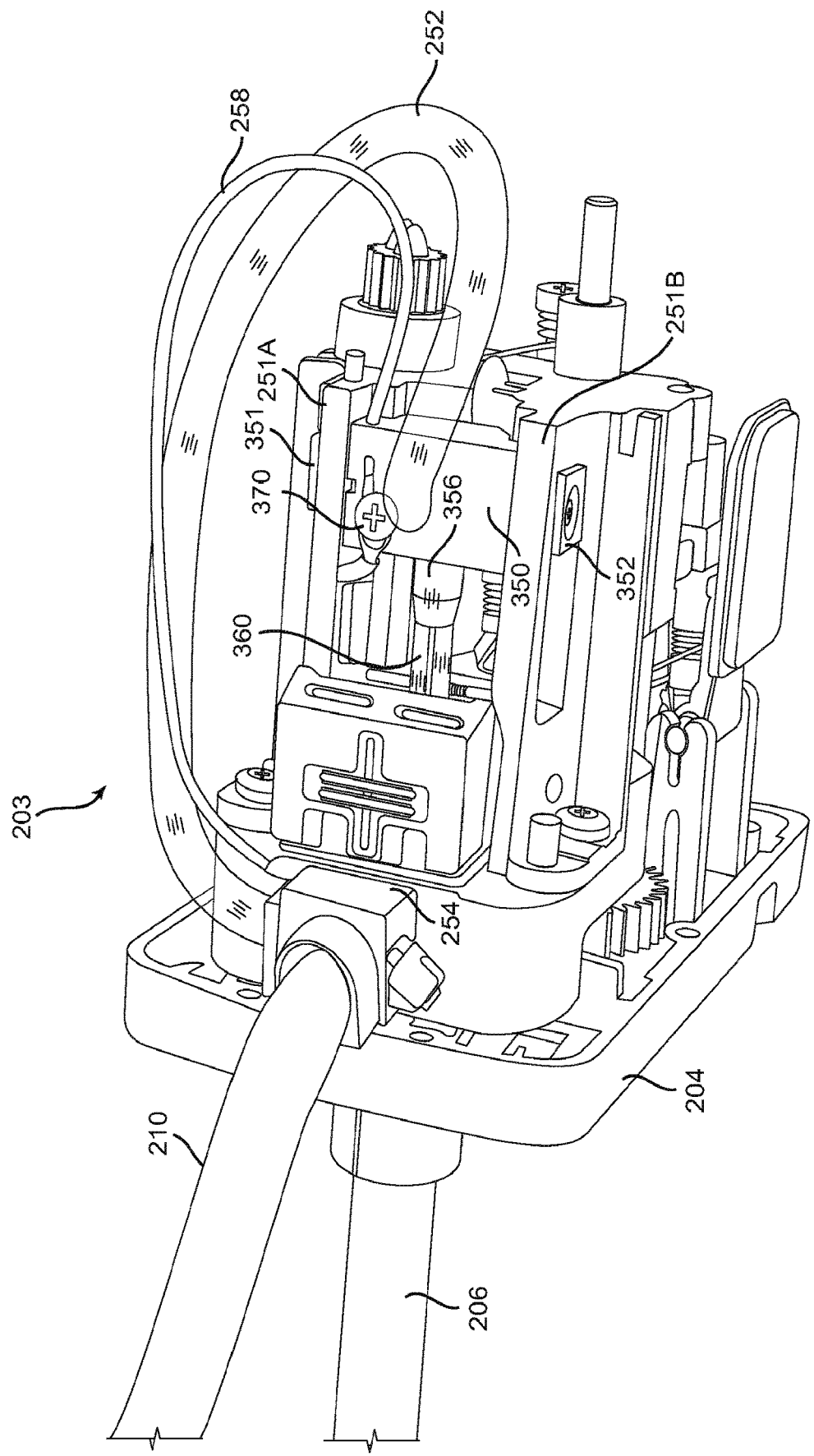

In this embodiment, a central portion of wire 253 (shown in FIG. 3D) is coupled to block 350. Also, first and second ends of wire 253 are wrapped around actuator 250B in an opposite direction (i.e., one end is wrapped around actuator 250B in direction A3 and the other end is wrapped around actuator 250B in a direction B3). In this way, when actuator 250B is rotated in a first direction (e.g., A3), a first end of wire 253 is further wrapped around actuator 250B and a second end of wire 253 is unwrapped from around actuator 250B, causing block 350 to slide in a distal direction, as shown in FIG. 7A. When actuator 250B is rotated in a second direction (e.g., B3), the first end of wire 253 is unwrapped from around actuator 250B and the second end of wire 256 is further wrapped around actuator 250B, causing block 350 to slide in a proximal direction, as shown in FIG. 7B.

Tube receiving member 358 is configured to receive an end of port 252. It is to be appreciated that flexible plastic tube 360 replaces tube 272 in the present embodiment. A distal end of the tube 360 is coupled to tip 208 and a proximal end of tube 360 is coupled to tube receiving member 356. Tube 360 is configured to be stretchable along the longitudinal axis defined by shaft 206 to accommodate the proximal and distal movements of block 350 within brackets 251A, 251B. Internal to block 350, tube receiving members 356, 358 are connected via a channel or passageway. In this way, gas is provided via a gas source through gas port 252 and into tube 360 via the internal channel connecting members 356, 358. Gas is further provided from tube 360 to tip 208.

Figure 7C:
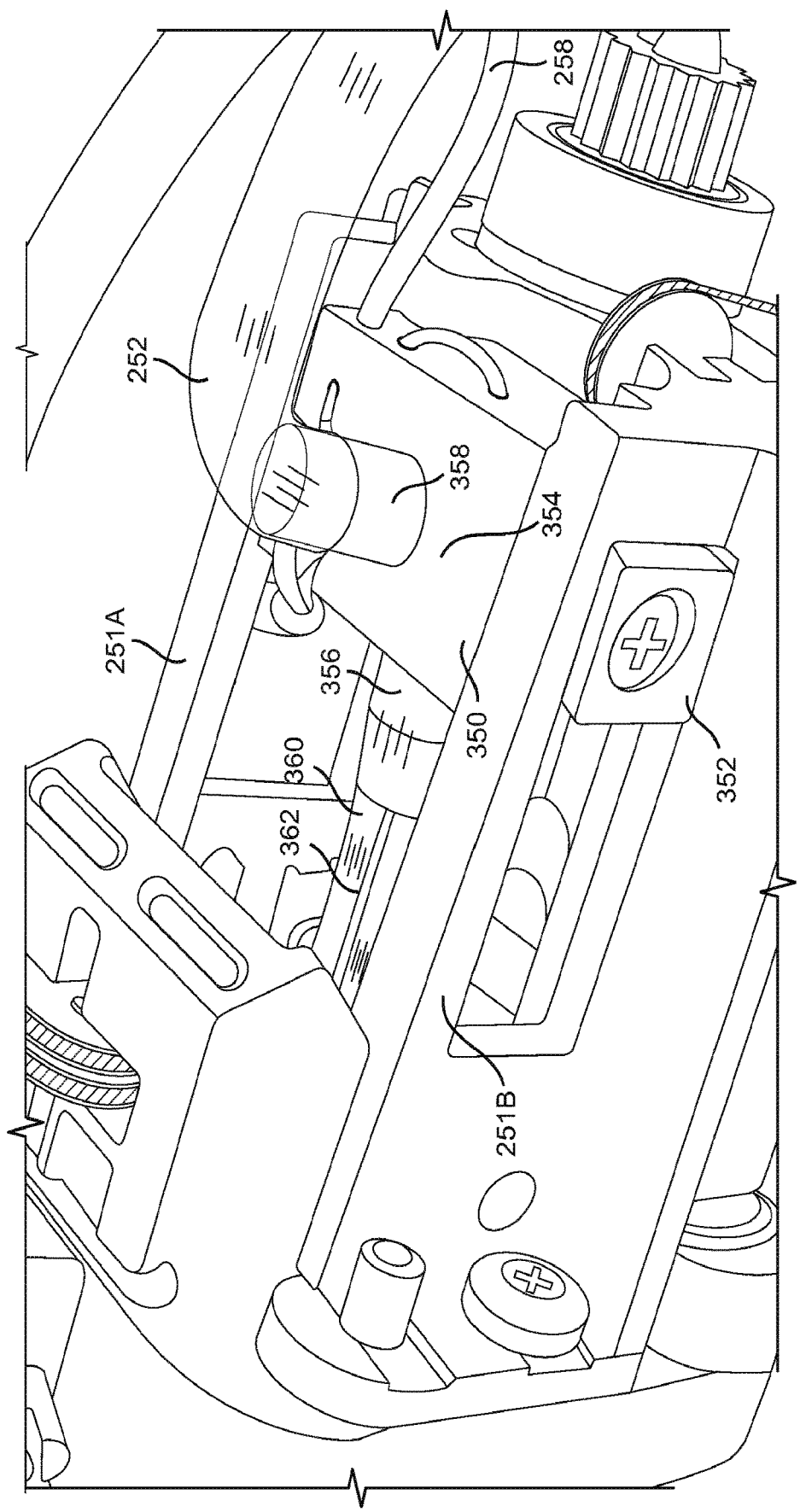

In one embodiment, wire 270 is disposed through tube 360, where a distal end of wire 270 is coupled to electrode 240. The proximal end of wire 270 is disposed through a hollow interior of tube receiving member 356 and coupled to cable 258, for example, via a conducting screw 370. In this way, when block 350 slides in a distal direction (as shown in FIG. 7A), wire 270 is advanced in a distal direction to extend electrode 240. When block 250 slides in a proximal direction (as shown in FIGS. 7B, 7C), wire 270 is retracted in a proximal direction to retract electrode 240.

In another embodiment, a wire 362 replaces wire 270. In one embodiment, wire 362 is a flexible stainless steel string with Teflon coating. Wire 362 is disposed through tube 360, where a distal end of wire 362 is coupled to electrode 240 and a proximal end of wire 362 enters the interior of block 350 and is coupled to cable 258, e.g., via screw 370. Wire 362 is configured to conduct electrosurgical energy provided from cable 258 (via an ESU) to electrode 240. Unlike wire 270, wire 362 is only configured for pulling electrode 240 in a proximal direction. In this embodiment, a spring (not shown) is disposed within tip 208 and biases electrode 240 in a distal direction, such that, electrode 240 is in an extended position (as described above) unless it is pulled on by wire 362. In this way, actuator 250B may be rotated in a first direction to slide block 350 in a proximal direction (as shown in FIGS. 7B, 7C) to pull wire 362 in a proximal direction, such that, electrode 240 is retracted into tip 208. Actuator 250B may be rotated in a second direction to slide block 350 in a distal direction (as shown in FIG. 7A), thereby, releasing the tension in wire 362 and allowing electrode 240 to be biased by the spring in tip 208 toward an extended position.

It is to be appreciated that although tubes 272 and 360 are shown and described as tubes including a single interior channel or lumen for providing a single gas to tip 208, in another embodiment of the present disclosure, tubes 272 and/or 360 may be configured as multi-lumen or multi-channel tubes for providing two or more gases to tip 208. In this embodiment, gas port 252 and cable 210 are each configured to provide two or more gases to the multi-lumen tubes 272 and/or 360, where each gas provided corresponds to a different lumen or channel of tubes 272 and/or 360. In another embodiment, one of the channels or lumens of the multi-lumen tubes 272 and/or tube 360 may be coupled to a source providing air-suction. In this way, tip 208 may be configured to also provide aspiration to a surgical site as desired.

As stated above, assembly 203 may include or be coupled to at least one processor configured to control the speed and direction of rotations of each of the motors coupled to actuators 250A-D, thus, also controlling the speed and direction of rotations of each of actuators 250A-D. The processor may include a mapping to the amount (i.e., fraction and/or number of revolutions) that each of actuators must be rotated to create the desired movement, orientation, extension, and retraction of electrode 240. It is to be appreciated that the processor may be included in assembly 203, or alternatively, may be external to assembly 203.

In one embodiment, apparatus 200 may be controllable via a separate peripheral device coupled to the processor described above. For example, the movement of robotic tip 208 may be controllable via a mouse, keyboard, joystick, or other input-receiving device coupled to the processor and apparatus 200. In one embodiment, the input receiving device may be a device that tracks the hand, wrist, and finger movements of the user. In this embodiment, the movements of the user's hand, wrist, and finger may be tracked and mapped (e.g., via a processing device as described above) to the appropriate rotations of actuators 250, such that, robotic tip 208 mimics the movements of the user. The input-receiving devices described above may be coupled to a processing device (e.g., a computer, a processor of ESU 12, and/or a processor of apparatus 200) configured to control actuators 250 of apparatus 200 and/or the motors coupled to actuators 250.

The processor and input receiving device may also be in communication with ESU 12 and the gas supply to control the plasma generation of electrode 240. For example, the processor may be configured to send a signal to ESU 12 and/or the gas supply in response to one or more inputs received from the input-receiving device to receive electrosurgical energy and/or gas via cable 210 to be provided to tip 208 to generate plasma or be used in electrosurgical cutting. For example, the input receiving device may include one or more foot pedals or buttons to activate different modes that ESU 12 is capable of (described above). For example, a first foot pedal may be configured to activate J-Plasma mode when pressed, while a second foot pedal may be configured to activate Cool-Coag™.

As stated above, in one embodiment, shaft 206 is made of a rigid material, such as, but not limited to, carbon fiber. In this embodiment, tip 208 of apparatus 200 may be inserted through a cannula or trocar for use in various surgical applications, such as, laparoscopic surgery. Since, as described above, tip 208 is configured to be manipulated as desired to achieve a plurality of orientations and positions relative to shaft 206 from a distance via the rotations of actuators 250A-D, tip 208 does not require a separate device or mechanism, e.g., forceps, to interact with tip 208 to control the orientations and positions of tip 208 during surgical applications. Since, no additional devices, such as forceps, are required to control the orientation and movement of tip 208, a cannula or trocar of smaller diameter than normally used may be used with electrosurgical apparatus 200 (since only shaft 206 and tip 208 is required to pass through the cannula or trocar) and an incision of a smaller diameter than normal may be created on the patient.

It is to be appreciated that the various features shown and described are interchangeable, that is a feature shown in one embodiment may be incorporated into another embodiment.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. An electrosurgical apparatus comprising:
an assembly including at least one actuator;
a shaft including a proximal end, a distal end, and a hollow interior, the proximal end of the shaft coupled to the assembly;
a tip including an electrode housing, the electrode housing including a proximal end and a distal end, an electrode being disposed through the distal end of the electrode housing;
a hinging mechanism coupling the proximal end of the electrode housing to the distal end of the shaft, the hinging mechanism including at least two hinging members that enable three dimensional pivoting of the electrode housing relative to the shaft, each hinging member including an aperture therethrough;
a flexible tube including a proximal end and a distal end, the flexible tube disposed through the hollow interior of the shaft, the distal end of the flexible tube disposed through the apertures of the at least two hinging members and coupled to the proximal end of electrode housing and the proximal end of the flexible tube coupled to the assembly and configured to receive a gas to be provided to the electrode housing;
a conductive wire disposed in the flexible tube, the conductive wire including a proximal end and a distal end, the proximal end of the conductive wire coupled to a source of electrosurgical energy via the assembly, the distal end of the conductive wire disposed through the apertures of the at least two hinging members and coupled to the electrode to provide electrosurgical energy to the electrode; and
a plurality of pulling mechanisms, each of the plurality of pulling mechanisms disposed through the hollow interior of the shaft and including a proximal end and a distal end, the proximal end of each of the plurality pulling mechanisms coupled to a respective one of the at least one actuator and the distal ends of each of the plurality of pulling mechanisms coupled to the proximal end of the electrode housing,
wherein the at least one actuator is configured to be rotated to selectively pull one or more of the plurality of pulling mechanisms in a proximal direction to pivot the tip relative to the shaft via the hinging mechanism, and
wherein the conductive wire is slidable within the flexible tube and the proximal end of the conductive wire is coupled to a second actuator disposed in the assembly, the second actuator configured to be rotated to control the extension of the electrode past the distal end of the electrode housing and retraction of the electrode within the distal end of the electrode housing.

2. The electrosurgical apparatus of claim 1, wherein the hinging mechanism includes a first hinging member and a second hinging member, the first and second hinging members hingedly coupled to each other such that, responsive to the selective pulling of one or more of the plurality of pulling mechanisms, the tip is pivoted relative to the shaft along a first two-dimensional plane.

3. The electrosurgical apparatus of claim 2, wherein the hinging mechanism includes a third hinging member, the third hinging member hingedly coupled to the second hinging member such that, responsive to the selective pulling of one or more of the pulling mechanisms, the tip is pivoted relative to the shaft along a second two-dimensional plane.

4. The electrosurgical apparatus of claim 3, wherein the at least one actuator includes a first actuator and a third actuator and the plurality of pulling mechanisms include first, second, third, and fourth pulling mechanisms, the proximal ends of the first and second pulling mechanisms coupled to the first actuator such that when the first actuator is rotated, one of the first or second pulling mechanisms is pulled in a proximal direction and tension from the other of the first or second pulling mechanisms is released enabling the other of the first or second pulling mechanisms to travel in a distal direction, the proximal ends of the third and fourth pulling mechanisms coupled to the third actuator such that when the third actuator is rotated, one of the third or fourth pulling mechanisms is pulled in a proximal direction and tension from the other of the third or fourth pulling mechanisms is released enabling the other of the third or fourth pulling mechanisms to travel in a distal direction.

5. The electrosurgical apparatus of claim 4, further comprising a fourth actuator, the fourth actuator coupled to the shaft such that rotation of the fourth actuator rotates the shaft relative to the assembly, wherein when the shaft is rotated, the tip is rotated.

6. The electrosurgical apparatus of claim 5, wherein each of the at least one actuators is coupled to a corresponding motor, each motor is controllable via at least one processor and at least one input receiving device to selectively rotate one or more of the actuators to pivot the tip relative to the shaft, rotate the tip and shaft relative to the assembly, and/or extend or retract the electrode relative to the distal end of the electrode housing.

7. The electrosurgical apparatus of claim 1, wherein when equal tension is maintained in each of the plurality of pulling mechanisms, the tip is colinear relative to the shaft.

8. The electrosurgical apparatus of claim 1, wherein each of the plurality of pulling mechanisms includes a first wire, a second wire, and a rigid linear member, the first wire coupled to the proximal end of the electrode housing, the rigid linear member coupling the first wire to the second wire, and the second wire coupled to the at least one actuator.

9. The electrosurgical apparatus of claim 1, wherein when the electrode is extended past the distal end of the electrode housing or the electrode is retracted within the electrode housing, the electrode is energized via the conductive wire and gas is provided to the electrode housing to form plasma.

10. The electrosurgical apparatus of claim 1, wherein the electrode is extended past the distal end of the electrode housing for mechanical cutting.

11. The electrosurgical apparatus of claim 1, wherein the electrode is extended past the distal end of the electrode housing and the electrode is energized via the conductive wire for electrosurgical cutting.

12. The electrosurgical apparatus of claim 1, further comprising a sliding member slidably mounted within the assembly, the sliding member coupled to the distal end of the conductive wire and to the second actuator, wherein, responsive to the rotation of the second actuator in a first direction, the sliding member is configured to pull the conductive wire in the proximal direction to retract the electrode within the distal end of the electrode housing.

13. The electrosurgical apparatus of claim 12, further comprising a spring disposed in the electrode housing, the spring configured to bias the electrode in a distal direction past the distal end of the electrode housing.

14. The electrosurgical apparatus of claim 12, wherein, responsive to the rotation of the second actuator in a second direction, the sliding member is configured to extend the conductive wire in a distal direction to extend the electrode past the distal end of the electrode housing.

15. The electrosurgical apparatus of claim 12, wherein the sliding member is coupled to an external gas source and coupled to the flexible tube, the sliding member is configured to provide the gas from the external gas source to the electrode via the flexible tube.

16. The electrosurgical apparatus of claim 15, wherein the sliding member is coupled to the electrosurgical energy source and the sliding member is configured to provide electrosurgical energy to the conductive wire.

17. The electrosurgical apparatus of claim 1, further comprising a third actuator, the third actuator coupled to the shaft such that rotation of the third actuator rotates the shaft relative to the assembly, wherein when the shaft is rotated, the tip is rotated.

18. The electrosurgical apparatus of claim 1, wherein the electrode is configured as one of an electrically conducting blade or an electrically conductive needle.

19. The electrosurgical apparatus of claim 1, wherein the at least one actuator is configured to be coupled to at least one motor for rotating the at least one actuator, the at least one motor is configured to be controlled via at least one processor and at least one input receiving device.

20. The electrosurgical apparatus of claim 1, wherein the plurality of pulling mechanisms are disposed between an exterior of the flexible tube and an inner wall of the shaft.

21. An electrosurgical apparatus comprising:
an assembly including at least one actuator;
a rigid shaft including a proximal end, a distal end, and a hollow interior, the proximal end of the shaft coupled to the assembly;
a tip including an electrode housing, the electrode housing including a proximal end and a distal end, the distal end of the electrode housing including a generally cylindrical ceramic insert having diametrically opposed slots disposed on an inner circumference of the ceramic insert configured to slidably receive portions of an electrically conducting blade electrode such that the ceramic insert and the blade electrode are fixed rotationally with respect to the electrode housing, the blade electrode being disposed through the distal end of the electrode housing;

a hinging mechanism coupling the proximal end of the electrode housing to the distal end of the shaft, the hinging mechanism including at least two hinging members that enable three dimensional pivoting of the electrode housing relative to the shaft, each hinging member including an aperture therethrough;

a flexible tube including a proximal end and a distal end, the flexible tube disposed through the hollow interior of the shaft, the distal end of the flexible tube disposed through the apertures of the at least two hinging members and coupled to the proximal end of electrode housing and the proximal end of the flexible tube coupled to the assembly and configured to receive a gas to be provided to the electrode housing;

a conductive wire disposed in the flexible tube, the conductive wire including a proximal end and a distal end, the proximal end of the conductive wire coupled to a source of electrosurgical energy via the assembly, the distal end of the conductive wire disposed through the apertures of the at least two hinging members and coupled to the blade electrode to provide electrosurgical energy to the blade electrode; and a plurality of pulling mechanisms, each of the plurality of pulling mechanisms disposed through the hollow interior of the shaft and including a proximal end and a distal end, the proximal end of each of the plurality pulling mechanisms coupled to a respective one of the at least one actuator and the distal ends of each of the plurality of pulling mechanisms coupled to the proximal end of the electrode housing, wherein the at least one actuator is configured to be rotated to selectively pull one or more of the plurality of pulling mechanisms in a proximal direction to pivot the tip relative to the shaft via the hinging mechanism, and wherein the conductive wire is slidable within the flexible tube and the proximal end of the conductive wire is coupled to a second actuator disposed in the assembly, the second actuator configured to be rotated to control the extension of the blade electrode past the distal end of the electrode housing and retraction of the blade electrode within the distal end of the electrode housing.

\* \* \* \* \*